US006197568B1

(12) United States Patent
Marks et al.

(10) Patent No.: US 6,197,568 B1
(45) Date of Patent: *Mar. 6, 2001

(54) METHOD AND COMPOSITIONS FOR ISOLATION, DIAGNOSIS AND TREATMENT OF POLYANION-BINDING MICROORGANISMS

(75) Inventors: Rory M. Marks, Ann Arbor, MI (US); Yaping Chen, San Diego, CA (US); Terence Maguire, Waverly Dunedin (NZ); Robert J. Linhardt, Iowa City, IA (US)

(73) Assignee: The Regents of the University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/123,770

(22) Filed: Jul. 28, 1998

Related U.S. Application Data

(60) Provisional application No. 60/053,828, filed on Jul. 29, 1997.

(51) Int. Cl.[7] ............................ C12Q 1/70; A61K 39/29; A61K 31/70; A01N 43/04; C12N 7/02
(52) U.S. Cl. .............................. 435/239; 435/5; 435/7.1; 435/7.8; 435/29; 435/803; 435/948; 424/185; 424/193.1; 424/196.11; 424/197.11; 424/279.1; 514/23; 514/54; 514/55; 514/56; 514/57; 514/58; 514/59; 514/60; 514/61; 514/62
(58) Field of Search .................................. 435/7.1, 5, 7.8, 435/29, 239, 803, 948; 424/185.1, 196.11, 197.11, 193.1, 279.1; 514/23, 54–62

(56) References Cited

U.S. PATENT DOCUMENTS 5,866,322 * 2/1999 Jou et al. .................................. 435/5

OTHER PUBLICATIONS

Anderson, R et al. "Correlation of E protein binding with cell susceptibility to dengue 4 virus infection" *Journal of General Virology* (1992), vol. 73, pp. 2155–2159.

Andrews, BS et al. "Replication of Dengue and Junin viruses in cultured rabbit and human endothelial cells" *Infection and Immunity* (Jun. 1978), vol. 20, No. 3, pp. 776–781.

Aruffo, A et al. "CD44 is the principal cell surface receptor for hyaluronate" *Cell* (Jun. 29, 1990) vol. 61, pp. 1303–1313.

Baeuerle PA and WB Huttner "Chlorate–A Potent Inhibitor of Protein Sulfation in Intact Cells" *Biochemical and Biophysical Research Communications* (Dec. 15, 1986) vol. 141, No. 2.

Bame, KJ and JD Esko "Undersulfated Heparan Sulfate in a Chinese Hamster Ovary Cell Mutant Defective in Heparan Sulfate N–Sulfotransferase" *The Journal of Biological Chemistry* (May 15, 1989) vol. 264, No. 14.

Bernfield, M et al. "Biology of the Syndecans: A family of transmembrane heparan sulfate proteoglycans" *Annual Review of Cell Biology* (1992) vol. 8, pp. 365–393.

Bork, P et al. "The Immunoglobulin Fold: Structural Classification, Sequence Patterns and Common Core" *J. Mol. Biol.* (1994) vol. 242, pp. 309–320.

Brandt, WE et al. "Effect of passage history on Dengue–2 Virus Replication in Subpopulations of Human Leukocytes" *Infection and Immunity* (Nov. 1979) vol. 26, pp. 534–541.

Cardin, AD and HJR Weintraub "Molecular Modeling of Protein–Glycosaminoglycan Interactions" *Arteriosclerosis* (Jan./Feb. 1989) vol. 9. No. 1, pp. 21–32.

Cecilia, D and EA Gould "Nucleotide Changes Responsible for Loss of Neuroinvasiveness in Japanese Encephalitis Virus Neutralization–Resistant Mutants" *Virology* (1991), vol. 181, pp. 70–77.

Chen, BPC and T Hai "Expression vectors for affinity purification and radiolabeling of proteins using *Eschdrichia coli* as host" *Gene* (1994) vol. 130, pp. 73–75.

Chen, et al. "Demonstration of Binding of Dengue Virus Envelope Protein to Target Cells" *Supplement to the American Journal of Tropical Medicine and Hygiene* (1994) vol. 55, No. 2 pp. 269–270, abstract 517.

Chen, Y et al. "Demonstration of Binding of Dengue Virus Envelope Protein to Target Cells" (Dec. 1996) *Journal of Virology.* vol. 70, No. 12, pp. 8765–8772.

Chen, Y et al. "Dengue virus infectivity depends on envelope protein binding to target cell heparan sulfate" (Aug. 1997) *Nature Medicine,* vol. 3, No. 8, pp. 866–871.

Chen, W and T Maguire "Nucleotide sequence of the envelope glycoprotein gene of a dengue–2 virus isolated during an epidemic of benign dengue fever in Tonga in 1974" *Nucleic Acids Research* (1990) vol. 18, No. 19, p. 5889.

(List continued on next page.)

Primary Examiner—Marianne P. Allen
Assistant Examiner—Mary K Feman
(74) Attorney, Agent, or Firm—Brinks Hofer Gilson & Lione

(57) ABSTRACT

Methods and compositions for the isolation, diagnosis and treatment of microorganisms such as flaviviruses and other hemorrhagic fever viruses are based on the sulfated polyanion-dependent interaction of flaviviruses and hemorrhagic fever viruses, in particular dengue virus, with target cells. The cellular receptors targeted by these viruses have been identified as sulfated polyanionic glycoproteins, that include highly sulfated heparan sulfate glycosaminoglycans for some target cell types, and as a sulfated mucin on vascular endothelium. Compounds such as heparin, highly sulfated heparan sulfate, and synthetic polyanions such as Suramin, inhibit the interaction between the microorganisms and target cells, thereby disrupting the infective process.

10 Claims, 13 Drawing Sheets

OTHER PUBLICATIONS

Daughaday, CC et al. "Evidence for two mechanisms of dengue virus infection of adherent human monocytes; Trypsin–sensitive virus receptors and trypsin–resistant immune complex receptors" *Infection and Immunity* (May 1981) vol. 32, No. 2, pp. 469–473.

Davis, BD et al. "The Nature of Viruses: Assay of Viruses" *Principles of Microbiology and Immunology* (1967) pp. 664–671.

Deubel, V., et al. "Processing, secretion, and immunoreactivity of carboxy terminally truncated dengue–2 virus envelope proteins expressed in insect cells by recombinant baculoviruses" *Virology* (1991) 180:442–447.

Elder, J. H. et al. "Endo–beta–N–acetylglucosaminidase F: Endoglycosidase from Flavobacterium. meningosepticum that cleaves both high–mannose and complex glycoproteins." *Proc. Natl. Acad. Sci.* (USA) (1982) 79:4540–4544.

Esko, J. D. et al. "Animal cell mutants defective in glycosaminoglycan biosynthesis" *Proc. Nati. Acad. Sci.* (USA) (1985) 82:3197–3201.

Esko, J. D. et al. "Inhibition of chondroitin and heparan sulfate biosynthesis in Chinese hamster ovary cell mutants defective in galactosyltransferase" *1. J. Biol. Chem.* (1985) 262:12189–95.

Faham, S. et al. "Heparin structure and interactions with basic fibroblast growth factor" *Science* (1996) 271:1116–20.

Fromm, J. R. et al. "Differences in the interaction of heparin with arginine and lysine and the importance of these basic amino acids in the binding of heparin to acidic fibroblast growth factor" *Arch Biochem Biophys.* (1995) 323:279–87.

Grattage, L. P. et al. "Effects of PMA, cytokines and dexamethasone on the expression of cell surface Fc receptors and mRNA in U937 cells" *Immunology and Cell Biology* (1992) 70:97–105.

Halstead, S. B. et al. "Studies on the pathogenesis of dengue infection in monkeys. 1. Clinical laboratory responses to primary infection" *J. Infect. Dis.* (1973) 128:7–14.

Halstead, S. B. "Pathogenesis of dengue: Challenges to molecular biology" *Science* (1988) 239:476–486.

Halstead, S. B. "Antibody, macrophages, dengue virus infection, shock, and hemorrhage: a pathogenetic cascade" *Rev. Infect. Dis.* (1989) 11:S830–S839.

Halstead, S. B. "The XXth century dengue pandemic: need for surveillance and research" *World Health Stat Q.* (1992) 45:292–298.

Hase, T. et al. "Flavivirus entry into cultured mosquito cells and human peripheral blood monocytes" *Arch. Virol.* (1989) 104:129–143.

He, R.–T. et al. "Antibodies that block virus attachment to Vero cells are a major component of the human neutralizing antibody response against dengue virus type 2" *J. Med. Virol.* (1995) 45:451–461.

Henchal, E. A., and J. R. Putnak "The dengue viruses" *Clinical Microbiology Reviews* (1990) 3:376–396.

Holzmann, H. et al. "A single amino acid substitution in envelope protein E of tick–borne encephalitis virus leads to attenuation in the mouse model" *J. Virology* (1990) 64:5156–5159.

Imbert, J. L. et al. "Dengue virus infects mouse cultured neurons but not astrocytes" *J. Med. Virol.* (1994) 42:228–33.

Jackson, T. et al. "Efficient Infection of Cells in Culture by Type O Foot–and–Mouth Disease Virus Requires Binding to Cell Surface Heparan Sulfate" *J. Virology* (1996) 70:5282–5287.

Jaffe, E. A. "Culture and identification of large vessel endothelial cells." In E. A. Jaffe ed, *Biology of endothelial cells* Martinus Nihoff, The Hague (1984).

Jennings, A.D. et al. "Analysis of a yello fever virus isolated from a fatal case of vaccine–associated human encephalitis" *J. Infect. Dis.* (1994) 169:512–8.

Jiang, W. R. et al. "Single amino acid codon changes detected in louping ill virus antibody–resistant mutants with reduced neurovirulence" *J. Gen. Virology* (1993) 74:931–935.

Kurane, I. et al. "Dengue–2 virus infection of human mononuclear cell lines and establishment of persistent infections" *Arch Virol.* 110:91–101.

Lidholt, K. et al. "A single mutation affects both N–acetyl-glucosaminyltransferase and glucuronosyltransferase activities in a Chinese hamster ovary cell mutant defective in heparan sulfate biosynthesis" *Proc. Natl. Acad. Sci.* (USA) (1992) 89:2267–2271.

Lin, B. et al. "Localization of a neutrlization epitope on the envelope protein of dengue virust type2" *Virology* (1994) 202:885–890.

Linhardt, R J. "Analysis of glycogonjugates, pp. 17.13.17–17.13.32. In A. Varki (ed.), Current Protocols in Molecular Biology" *Wiley Interscience,* Boston (1994).

Linhardt, R. J. et al. "Heparin oligosaccharides—new analogs development and application" In Z.B. Witczak and K. A. Nieforth (ed.), Carbohydrates as Drugs. Marcel Dekker, New York (1997).

Lucia, H. L. et al. "Identification of dengue virus–infected cells in parrafin–embedded tissue using in situ polymerase chain reaction and DNA hybridization" *J. Virol. Methods* (1994) 48:1–8.

Maccarana, M. et al. "Domain structure of heparan sulfates from bovine organs" *J. Biol. Chem.* (196) 271:17804–17810.

McClain, D.S. et al. "Cell–specific kinetics and efficiency of herpes simplex virus type 1 entry are determined by two distinct phases of attachment" *Virology* (1994) 198:690–702.

Montgomery, R. I. et al. "Herpes simplex virus–1 entry into cells mediated by a novel member of the TNF/NGF receptor family" *Cell* (1996) 87:427–436.

Ortega–Barria, E. et al. "A novel T. cruzi heparin–binding protein promotes fibroblast adhesion and penetration of engineered bacteria and trypanosomes into mammalian cells" *Cell* (1991) 67:411–21.

Peitsch, M. C. "ProMod and Swiss–Model: Internet–based tools for automated comparative protein modelling" *Biochem Soc. Trans.* (1996) 24:274–279.

Porterfield, J.S. "Antibody–dependent enhancement of viral infectivity" *Adv. Virus Research* (1986) 31:335–355.

Raake, W. et al. "Anticoagulant and antithrombotic properties of synthetic sulfated bis–lactobionic acid amides" *Thromb Res.* (1989) 56:719–30.

Reed, L. J. et al. "A simple method of estimating fifty per cent end points" *Amer. J. Hygiene* (1938) 27:493–497.

Rey, F. A. et al. "The envelope glycoprotein from tick–borne encephalitis virus at 2 A resolution" *Nature* (1995) 375:291–8.

Rice, C. M. "Flaviviridae: the viruses and their replication", pp. 931–959. In B. N. Fields and D. M. Knipe A–17y and P. M. Howley (ed.), *Fields Virology 3rd edition,* vol. 1 Lippincott–Raven, Philadelphia (1996).

Rostand, K. S. et al. "Microbial adherence and invasion through proteoglycans" *Infect. Immun.* (1997) 65:1–8.

Ruoslahti, E. et al. "New perspectives in cell adhesion: RGD and integrins" *Science* (1987) 238:491–497.

Salzman, G. C. et al. "Cell classification by laser light scattering: identification and separation of unstained leukocytes" *Acta. Cytol.* (1975) 19: 374–377.

Sanchez, I. J. et al. "A single nucleotide change in the E protein of dengue virus 2 mexican strain affects neurovirulence in mice" *J. General Virology* (1996) 77:2541–2545.

Sahaphong, S. et al. "Electron microscopic study of the vascular endothelial cell in dengue hemorrhagic fever" *Southeast. Asian. J. Trop. Med. Pub. Health* (1980) 11:194–204.

Shao, H. et al. "cDNA cloning and characterization of a ligand for the Cek5 receptor protein–tyrosine kinase" *J. Biol. Chem.* (1994) 269:26606–26609.

Sternbergh, W. C. et al. "Heparinoids with low anticoagulant potency attenuate postischernic endothelial cell dysfunction" *J Vasc Surg.* (1995) 21:477–83.

Tarr, G. C. et al. "Chemically induced temperature–sensitive mutants of dengue virus type 2: comparison of temperature sensitivity in vitro with infectivity in suckling mice, hamsters, and rhesus monkeys" *Infect. Immun.* (1976) 13:688–695.

Thompson, L. D. et al. "Energetic characterization of the basic fibroblast growth factor—heparin interaction: identification of the heparin binding domain" *Biochemistry* (1994) 33:3831–3840.

Toida, T. et al. "Enzymatic preparation of heparin oligosaccharides containing antithrombin III binding sites" *J. Biol. Chem.* (1996) 271:32040–32047.

Toida, T. et al. "Structural differences in heparan sulfates from different tissues and species" *Biochemical Journal* (1997) 322:499–506.

Tyler, K. L. et al. "Pathogenesis of viral infections", pp. 173–217. In B. N. Fields and D. M. Knipe and P. M. Howley (ed.), *Fields Virology* 3rd edition, vol. 1. Lippincott–Raven, Philadelphia (1996).

Umemoto, J. et al. "Purification and properties of an endo–alpha–N–acetyl–D–galactosaminidase from Diplococcus pneurnoniae" *J. Biol. Chem.* (1977) 252:8609–8614.

Wimmer, E. "Introduction, pp. 1–13. In E. Winimer (ed.), "Cellular receptors for animal viruses vol. 1. *Cold Spring Harbor Laboratory Press,* New York (1994).

* cited by examiner

SEQUENCE LISTING

```
<160> NUMBER OF SEQ ID NOS: 10

<210> SEQ ID NO 1
<211> LENGTH: 27
<212> TYPE: PRT
<213> ORGANISM: Dengue virus

<400> SEQUENCE: 1

Lys Cys Arg Leu Arg Met Asp Lys Leu Gln Leu Lys Gly Met Ser Tyr
  1               5                  10                  15

Ser Met Cys Thr Gly Lys Phe Lys Ile Val Lys
             20                  25

<210> SEQ ID NO 2
<211> LENGTH: 26
<212> TYPE: PRT
<213> ORGANISM: Dengue virus

<400> SEQUENCE: 2

Gln Leu Lys Leu Asp Trp Phe Lys Lys Gly Ser Ser Ile Gly Gln Met
  1               5                  10                  15

Phe Glu Thr Thr Met Arg Gly Ala Lys Arg
             20                  25

<210> SEQ ID NO 3
<211> LENGTH: 42
<212> TYPE: PRT
<213> ORGANISM: Marburg virus

<400> SEQUENCE: 3

Lys Lys Gly Pro Ala Thr Thr Ala Pro Asn Thr Thr Asn Glu His Phe
  1               5                  10                  15

Thr Ser Pro Pro Pro Thr Pro Ser Ser Thr Ala Gln His Leu Val Tyr
             20                  25                  30

Phe Arg Arg Lys Arg Ser Ile Leu Trp Arg
         35                  40

<210> SEQ ID NO 4
<211> LENGTH: 16
<212> TYPE: PRT
<213> ORGANISM: Yellow fever virus
```

```
<400> SEQUENCE: 4

Lys Gly Thr Ser Tyr Lys Ile Cys Thr Asp Lys Met Phe Phe Val Lys
  1               5                  10                  15

<210> SEQ ID NO 5
<211> LENGTH: 17
<212> TYPE: PRT
<213> ORGANISM: Ebola virus

<400> SEQUENCE: 5

Gly Gly Arg Arg Thr Arg Arg Glu Ala Ile Val Asn Ala Gln Pro Lys
  1               5                  10                  15

Cys

<210> SEQ ID NO 6
<211> LENGTH: 32
<212> TYPE: PRT
<213> ORGANISM: Lassa virus

<400> SEQUENCE: 6

Lys Ser Cys Pro Lys Pro Pro His Arg Leu Asn His Met Gly Ile Cys
  1               5                  10                  15

Ser Cys Gly Leu Tyr Lys Gln Pro Gly Val Pro Val Lys Trp Lys Arg
                 20                  25                  30

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer direct to Dengue Virus

<400> SEQUENCE: 7
ctagctagcg atgcgctgca taggaatatc aaatagggga                        39

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:Synthetic
      Peptide Sequence for Heart Muscle Kinase Target
      Site

<400> SEQUENCE: 8

Arg Arg Ala Ser Val Gly Arg Arg Ala Ser Val
  1               5                  10

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:Synthetic
      antisense oligonucleotide primer

<400> SEQUENCE: 9
acctacagat gcacgtcgag atccaaaatc ccaggctgt                         39

<210> SEQ ID NO 10
<211> LENGTH: 42
<212> TYPE: DNA
<213> ORGANISM: Artificial Sequence
<220> FEATURE:
```

-continued

```
<223> OTHER INFORMATION: Description of Artificial Sequence:Synthetic
      antisense oligonucleotide primer

<400> SEQUENCE: 10
cggaagatct actgatgcac gacgacctac agatgcacgt cg                          42
```

METHOD AND COMPOSITIONS FOR ISOLATION, DIAGNOSIS AND TREATMENT OF POLYANION-BINDING MICROORGANISMS

This application claims priority from provisional application U.S. Serial No. 60/053,828, filed Jul. 29, 1997.

This invention was made with government support under grants HL52622, GM38060, AI33189, AR20557 and AR41703 awarded by the National Institutes of Health. The government has certain rights in the invention.

BACKGROUND OF THE INVENTION

Methods and compositions for the isolation, diagnosis and treatment of microorganisms such as flaviviruses and other hemorrhagic fever viruses are based on the sulfated polyanion-dependent interaction of the microorganisms with target cells. The cellular receptors used by flaviviruses and hemorrhagic fever viruses, in particular dengue virus, have been identified as sulfated polyanionic glycoproteins, that include highly sulfated heparan sulfate glycosaminoglycans for some target cell types, and as a sulfated mucin on vascular endothelium. Compounds such as heparin, highly sulfated heparan sulfate, and synthetic polyanions such as Suramin, inhibit the interaction between the virus and target cells, thereby disrupting the infective process.

The family of flaviviridae include pathogens causing disease in both humans and animals. Deleterious effects of the pathogens are of global health, agricultural, and economic significance. The viral family of flaviviruses includes members such as the arthropod-borne dengue virus that causes a serious febrile illness in humans. The failure to maintain programs to control the mosquito vector for dengue virus transmission has been associated with an alarming escalation of infection rates that is of increasing medical, public health, and military concern. It has been estimated that two and a half billion people in over 100 countries are at risk of infection, and there are a minimum of 20 million infections per year, mostly in children. There is no vaccine for dengue virus, few vaccines for other flaviviruses are available, and there is no specific or successful treatment for any flavivirus infection.

Dengue virus is a representative member of the family flaviviridae genus flavivirus, is also an arbovirus, and is also classified as one of a group of hemorrhagic fever viruses (HFV's) that cause prominent vascular pathology. Hemorrhagic fever viruses are an otherwise diverse grouping of viruses that include Yellow Fever virus (another flavivirus); the arenaviridae Lassa, Junin, and Machupo; bunyaviridae Rift Valley, Congo-Crimean, and Hantaan; and filoviridae Marburg and Ebola. Because these viruses share characteristics of short incubation, acute onset, debilitation and high mortality, and untreatability, they are considered likely choices for development of biological warfare agents. It is important that the molecular basis of the pathogenesis of these viruses be understood, and in particular that any common pathogenic features be exploited, in order to develop generic approaches to detection and treatment. An important unanswered question about the pathogenesis of dengue virus, other flaviviruses and other HFV's is the mechanism whereby they bind target cells. It has been difficult to find an answer to this question due to limitations inherent in investigations of these microorganisms. For example, because there is no valid animal model for dengue virus infection, studies of dengue pathophysiology usually involve infection of cultured cells, such as Vero cells.

The initial binding of a virus to a target cell is a critical determinant of cell and tissue tropism, and thus infectivity and pathogenesis. Binding occurs as a result of an adhesion receptor-like interaction between a viral ectodomain molecule and a corresponding co-receptor expressed on the surface of target cells. Little is understood about the pathogenesis of flavivirus or hemorrhagic fever virus infection, and there is no information about the molecular basis of the binding of any of these viruses to target cells. It has been suggested that infection of some cells may involve anti-viral antibody mediated immune-adherence; the Fc domain of antibody that is bound to virus may mediate binding to cells such as monocytes that express Fc receptors. However, this mechanism does not explain primary infection in patients without antibody, or infection of cells lacking Fc receptors.

Currently, viral diagnosis depends on indirect serological analysis (i.e. development of antibodies), or direct assessment of patient-derived specimens for the presence of virus (culture, molecular detection). Serology is probably the most sensitive diagnostic test, but the time required for development of significant titers of antibodies leads to delays in diagnosis. Direct assessment for the presence of virus is definitive, but often insensitive, probably due to inadequately low concentrations of virus in specimens. Elucidation of the binding mechanism of microorganisms such as flaviviruses, to target cells would facilitate diagnostic and therapeutic strategies.

SUMMARY OF THE INVENTION

Methods and compositions based on the interaction of microorganism ectodomain proteins with sulfated polyanions, in particular some glycosaminoglycans (GAGs) such as heparin and highly sulfated heparan sulfate, allow isolation, diagnosis and treatment of the microorganism. Suitable microorganisms include bacteria, flaviviruses and hemorrhagic fever viruses.

Flaviviruses have a relatively simple structure with only a single major external protein, the envelope protein. An aspect of the invention is that the cellular receptor utilized by flavivirus envelope proteins to bind to some target cells, as exemplified by dengue virus, is a highly sulfated type of heparan sulfate (HS). The cellular receptor on vascular endothelial cells is a related type of sulfated polyanionic glycoprotein, a mucin. The interaction between virus and host cell is a critical determinant of infectivity. Highly sulfated HS and heparin and synthetic polyanions, but not other glycosaminoglycans (GAGs), were effective competitive antagonists of dengue virus envelope protein binding to target cells. Pre-treatment of cells with GAG-lyases, and with the sulfation inhibitor sodium chlorate, prevented envelope protein binding. Mutant cell lines with defective GAG expression, including a mutant cell line specifically deficient only in HS expression, also failed to bind envelope protein. GAGs such as heparin and HS failed to competitively inhibit dengue virus envelope protein binding to endothelial cells, and treating endothelial cells with GAG-lyases also failed to inhibit subsequent binding of envelope protein, indicating that the endothelial receptor was not a GAG. However, treatment of endothelial cells with the mucin-specific lyase, O-sialoglycopeptidase did prevent subsequent envelope protein binding, indicating that the endothelial receptor was a mucin. Recombinant envelope protein bound to immobilized heparin, and eluted with 0.5 M NaCl, indicating a high affinity interaction.

Examination of the dengue virus envelope protein sequence revealed two GAG-binding motifs at the carboxy-terminus; the first could be structurally modeled and formed an unusual extended binding surface of basic amino acids, sufficiently large and accessible to interact with a GAG. Similar motifs were also identified in the envelope proteins of other flaviviridae and other hemorrhagic fever viruses. Many microorganisms including bacteria, protozoa and other viruses are known to utilize GAGs as binding targets, therefore, similar motifs are expected to be a general phenomenon. Heparin, highly sulfated HS, and the polysulfonate pharmaceutical Suramin effectively prevented dengue virus infection of target cells. Therefore, blockade of virus-target cell interactions is an effective strategy for treating flavivirus infections. This conclusion extends to all microorganisms.

In view of their common feature of vascular pathology, it is expected that other flaviviruses and hemorrhagic fever viruses all use the GAG-binding domains expressed in their envelope proteins, to bind to a similar vascular endothelial cell receptor. Supporting evidence consists of identifying putative GAG-binding domains in the peptide sequences of the envelope proteins of all flaviviruses examined and in four hemorrhagic fever viruses other than dengue virus: Yellow Fever, Ebola, Marburg and Lassa fever viruses.

An aspect of the invention is a method for isolating a microorganism such as a flavivirus by exploiting the polyanion-dependent interaction of the microorganism with target cells to remove the microorganism from a biological sample. In an illustrative example, a biological sample from which the microorganism is to be isolated is contacted with a polyanion in a fashion such that the microorganism adheres to the polyanion while other components of the biological sample do not adhere to the polyanion, thereby being separated from the microorganism.

The biological sample is a portion or derivative of an organism, including, for example, a blood, serum or tissue sample, washings from materials in contact with the organism, and cells or cell lines derived from the organism. Generally, the sample will be in the form of a fluid when contacted to the polyanion. The polyanion is generally attached to an inert matrix such as polymerized forms of agarose, cellulose, dextran, or polyacrylamide, which is retained within a column suitable for the passage of liquids for contact with the contents of the column.

Not only do methods of the present invention isolate a microorganism such as a virus, but the avid binding between the virus and a compound such as heparin is used to concentrate virus onto a solid phase, following which it can be released for further use. This reaction is very efficient, that is, virus can be concentrated from a very dilute concentration (concentrations too low to be detected by conventional means) to a concentration that is readily detectable. Concentration 100-fold above minimum detection limits was demonstrated for flavivirus, for example. An advantage is that essentially all the virus that is collected can be released for analysis.

Relevant to agricultural industry, research and biological warfare, potentially contaminated surfaces, personnel, and the like are analyzed by taking washings, collecting the microorganism such as a virus, by passage over, for example, immobilized-heparin, and analyzing the captured virus after being released. Methods of analysis known to those of skill in the art include culture, immunological analysis and molecular analysis.

Patients infected with microorganisms such as flaviviruses and hemorrhagic fever viruses have virus circulating freely in the bloodstream. In these cases, viral load is likely to be a significant pathogenic factor. An aspect of the invention is to treat these diseases by removing polyanion-binding viruses from the bloodstream by passing plasma over immobilized heparin. This is technically feasible and is similar to passing blood through a device to remove pathological mediators (e.g. as performed in cytophoresis, plasmaphoresis).

Treatment may be administered before exposure to the microorganism to prevent infection; after infection but before the development of symptoms to prevent occurrence of disease; or after the appearance of disease to prevent progression to more serious and possibly life-threatening forms of disease, and to ameliorate and shorten the disease process. Treatment consists of topical application of a polyanion to the skin in the form of a liquid, introduction to the airways and lungs in the form of an aerosolized liquid, ingestion of an orally bioavailable form of the polyanion, or systemic administration in the form of an intra-dermal, subcutaneous, intramuscular, or intravenous indictable form.

Uses for the methods and compositions of the present invention include:

i) Developing pharmaceuticals to treat infections caused by microorganisms including dengue virus, other flavivirus and other hemorrhagic fever virus.

ii) Developing vaccines to prevent infections by microorganisms such as dengue virus, other flavivirus and other hemorrhagic fever virus.

iii) Developing viral diagnostic aids e.g. the avid binding between dengue virus and heparin is exploited to generate agents that concentrate the virus onto a solid phase, as an aid for transport, culture, and molecular and immunologic diagnostic techniques.

iv) Development of gene therapy transfer vectors, based on the cell-targeting motifs discovered in the dengue virus envelope protein, having the potential for greatly improved targeting to vascular endothelium.

For gene therapy the envelope protein target-cell binding motif identified for dengue virus is used to target genes to endothelial cells or other target cells. The envelope protein is expressed on the surface of a virus-based gene-targeting vector, e.g. adenovirus, retrovirus, or expressed/synthesized protein is chemically derivatized to a non-biologic gene targeting module. The procedure is also followed using envelope protein target-cell binding motifs in microorganisms including bacteria, protozoa and other viruses.

Panels A–D: Competitive antagonists. Recombinant dengue 2 virus envelope protein was co-incubated with Vero cells in the presence of potential competitive antagonists, and the degree of binding was quantitated by flow cytometry. Abscissa: Competitive antagonist. Binding of envelope protein without antagonist is indicated by dengue Env column. Background binding (cells incubated with normal human IgG instead of envelope protein) is indicated by Control IgG column. Ordinate: Median fluorescence intensity derived from flow cytometry histograms for each sample.

A) Polysaccharides: Heparin, Heparan sulfate derived from bovine kidney (HS), Chondroitin sulfate (CS), Dermatan sulfate (DS), Keratan sulfate (KS), and Dextran sulfate (DexS), all at a concentration of 10 µg/ml.

B) Heparan Sulfate: highly sulfated liver-derived heparan sulfate (■■■), and normally sulfated testis-derived heparan sulfate (●■●).

C) Heparin oligosaccharides: Fully sulfated homogeneous di-, tetra-, hexa-, octa-, and decasaccharide, and a control decasaccharide containing the pentasaccharide antithrombin-III binding site, all at a concentration of 10 μg/ml.

D) Envelope protein binding to heparin: Recombinant envelope protein was radiolabeled with $^{32}$P, incubated with immobilized heparin, and bound envelope protein was eluted with a step-gradient of increasing concentrations of NaCl. Abscissa: Fraction number. Ordinate: Radioactivity (cpm×10$^4$)/fraction (●■●), [NaCl] in elution buffer (------).

Figure 2:
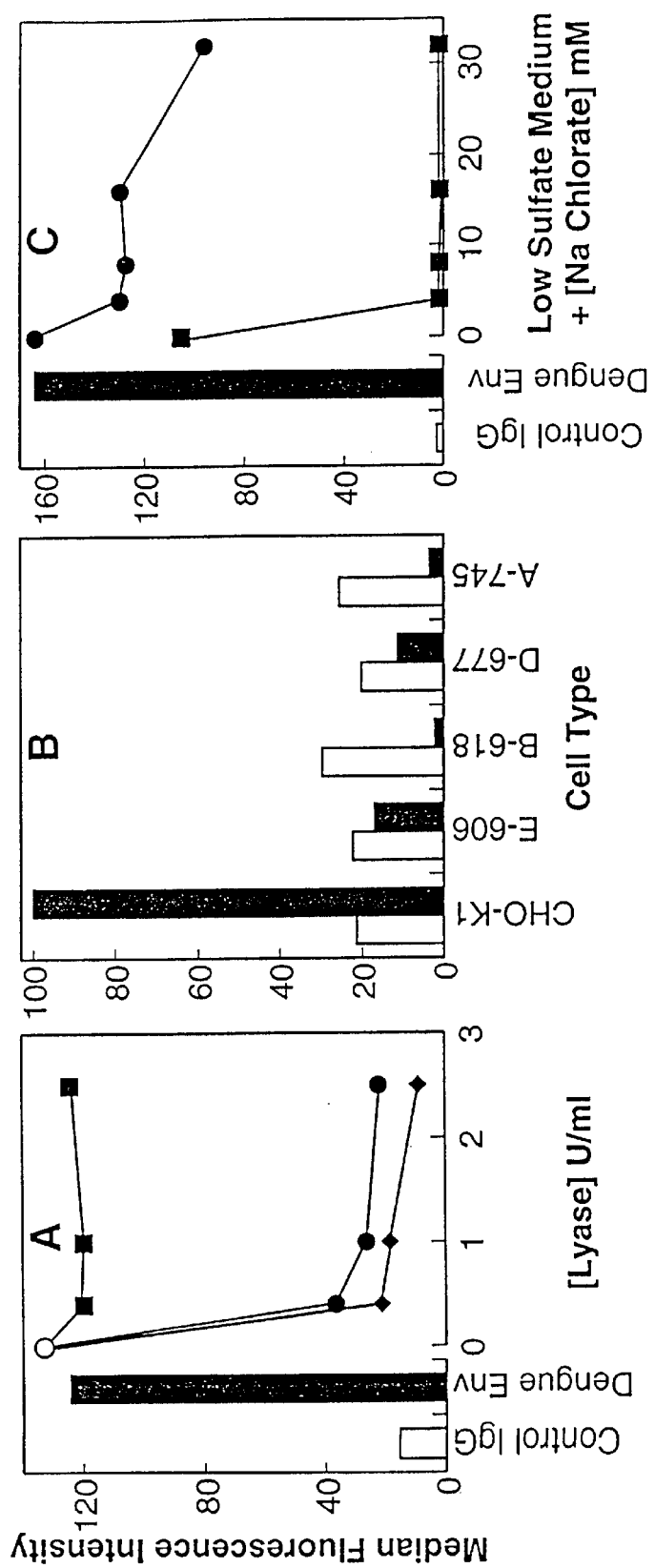

FIG. 2 shows role of cell-surface heparan sulfate in envelope protein binding.

Figure 1:
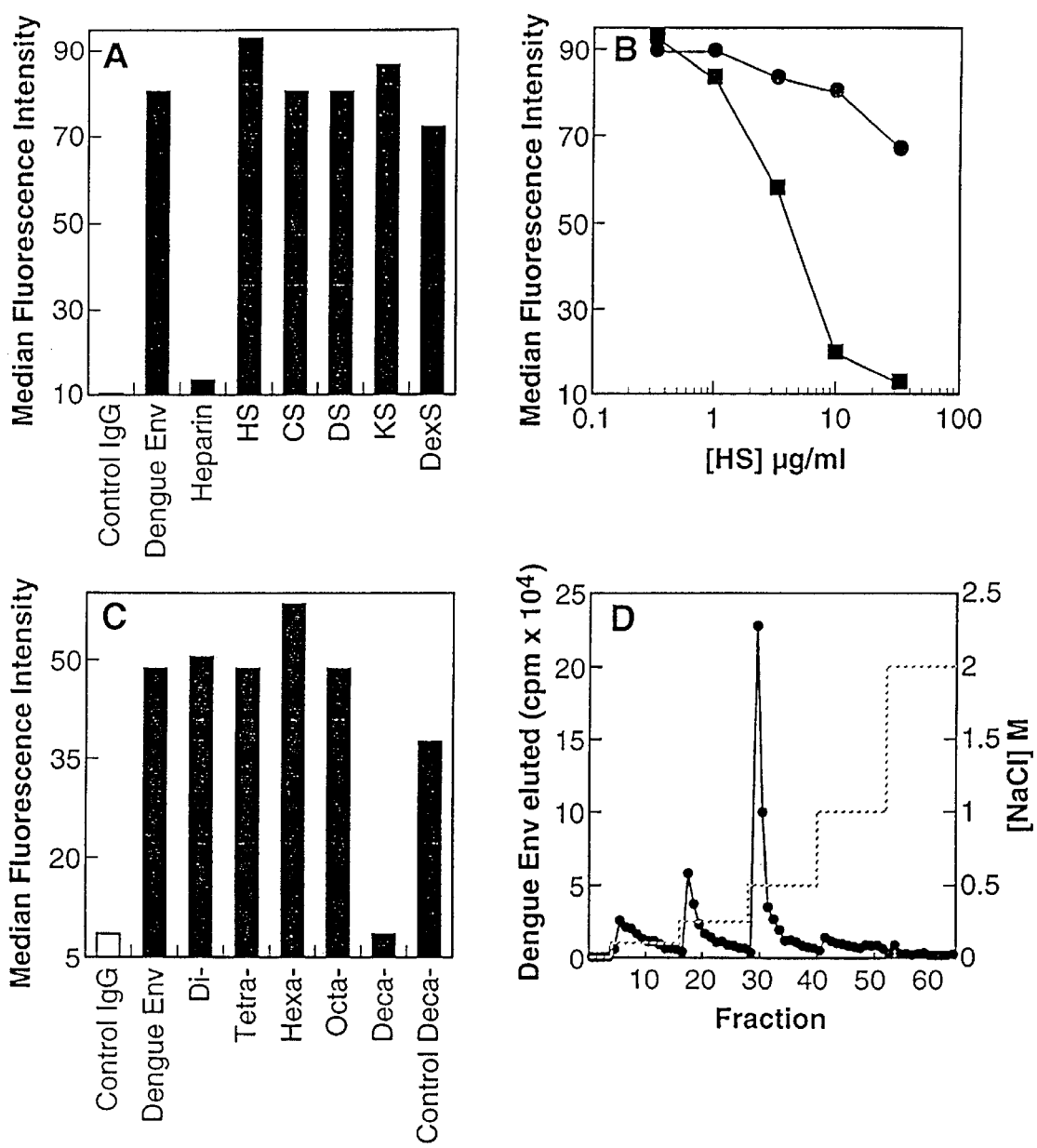
FIG. 1 illustrates the interaction of dengue virus envelope protein with GAGs.

A) GAG lyases. Cells were incubated with Chondroitin ABC lyase (■■■), Heparin lyase I (●■●) and Heparin lyase III (♦■♦), 0.4–2.5 U/ml, and envelope protein binding was assessed as described for FIG. 1. Abscissa: Binding of envelope protein to untreated cells is indicated by dengue Env column. Background binding of untreated cells is indicated by control IgG column. Envelope protein binding to mock digested cells (incubated in digestion buffer without enzyme) (O). Ordinate: Median Fluorescence Intensity derived from flow cytometry histograms for each sample.

B) CHO cell mutants with altered GAG expression. Envelope protein binding was assessed as described for FIG. 1. Abscissa: Cell type CHO-K1: parental cell source for mutants. PgsE-606: defective HS N-sulfotransferase with reduction of HS N-sulfation and subsequent reduction of iduronic acid formation, 2-O-sulfation, and 6-O-sulfation; pbsB-618: defective galactosyltransferase I with inhibition of chondroitin sulfate and HS biosynthesis; pgsD-677: completely deficient in HS synthesis, but increased accumulation of chondroitin sulfate; pgsA-745: deficient xylosyltransferase with global failure of GAG expression. Binding of envelope protein is indicated by a solid column. Background binding (cells incubated with normal human IgG instead of envelope protein) is indicated by an open column. Ordinate: Normalized median fluorescence intensity derived from flow cytometry histograms for each sample.

C) Dependence on cellular sulfation: Vero cells were cultured in normal medium, or low-sulfate medium for 48 hours, in the presence of the sulfation-inhibitor sodium chlorate (0–32 mM). Replicate cells were supplemented with sodium sulfate (2 mM) to assess the sulfation specificity of any inhibition observed. Envelope protein binding was assessed at the completion of the incubation period, as described for FIG. 1. Cell viability was not adversely affected by these treatments as indicated by unchanged flow cytometry light scatter. Abscissa: Binding of envelope protein to cells cultured in normal medium is indicated by dengue Env column. Background binding to cells cultured in normal medium is indicated by control IgG column. Cells incubated in low-sulfate medium and sodium chlorate (■■■). Cells incubated in low-sulfate medium and sodium chlorate, and further supplemented with sodium sulfate (●■●). Ordinate: Median fluorescence intensity derived from flow cytometry histograms for each sample.

Figure 3:
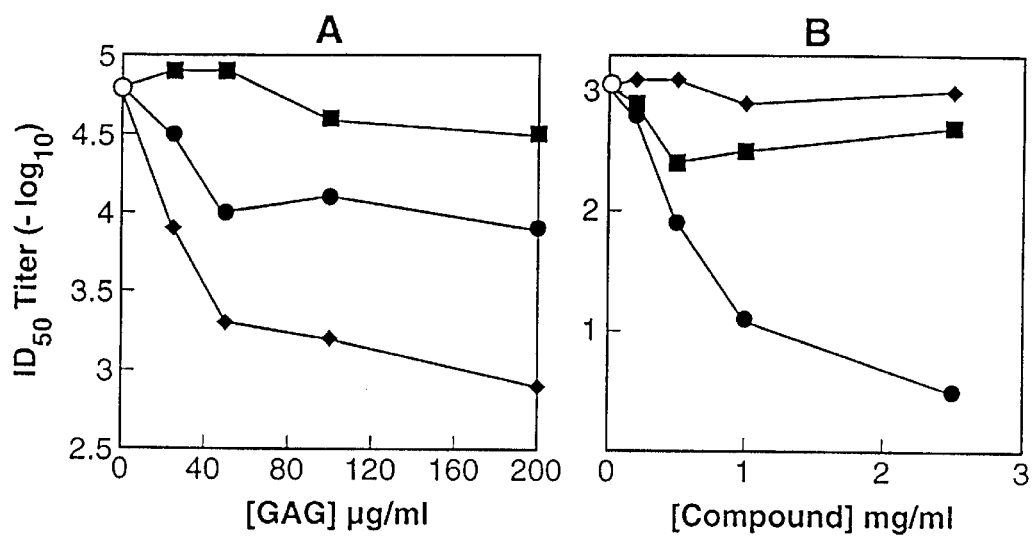

FIG. 3 shows inhibition of dengue virus infectivity by compounds that block envelope protein binding.

A) GAGs inhibit infection. Serial dilutions of dengue 2 New Guinea C strain virus were mixed with each GAG, and added to Vero cells for 5 minutes at 4° C. Non-bound virus was removed by washing, and the cells were cultured and observed for cytopathic effect for 7 days. Abscissa: GAG (O-200 μg/ml.); low-sulfate HS (■■■), highly sulfated HS (●■●), heparin (♦■♦), no inhibitor (O) Ordinate: ID$_{50}$ titer (–log$_{10}$ of dilution of virus at which 50% of wells demonstrated cytopathic effect).

B) Suramin inhibits infection. Polyanionic compounds were tested for activity in inhibiting dengue virus infection of Vero cells as described for panel A. Abscissa: compound (0–2.5 mg/ml); sulfated lactobionic acid (♦■♦), Astenose (■■■), Suramin (●■●), no inhibitor (O). Ordinate: ID$_{50}$ titer.

Figure 4:
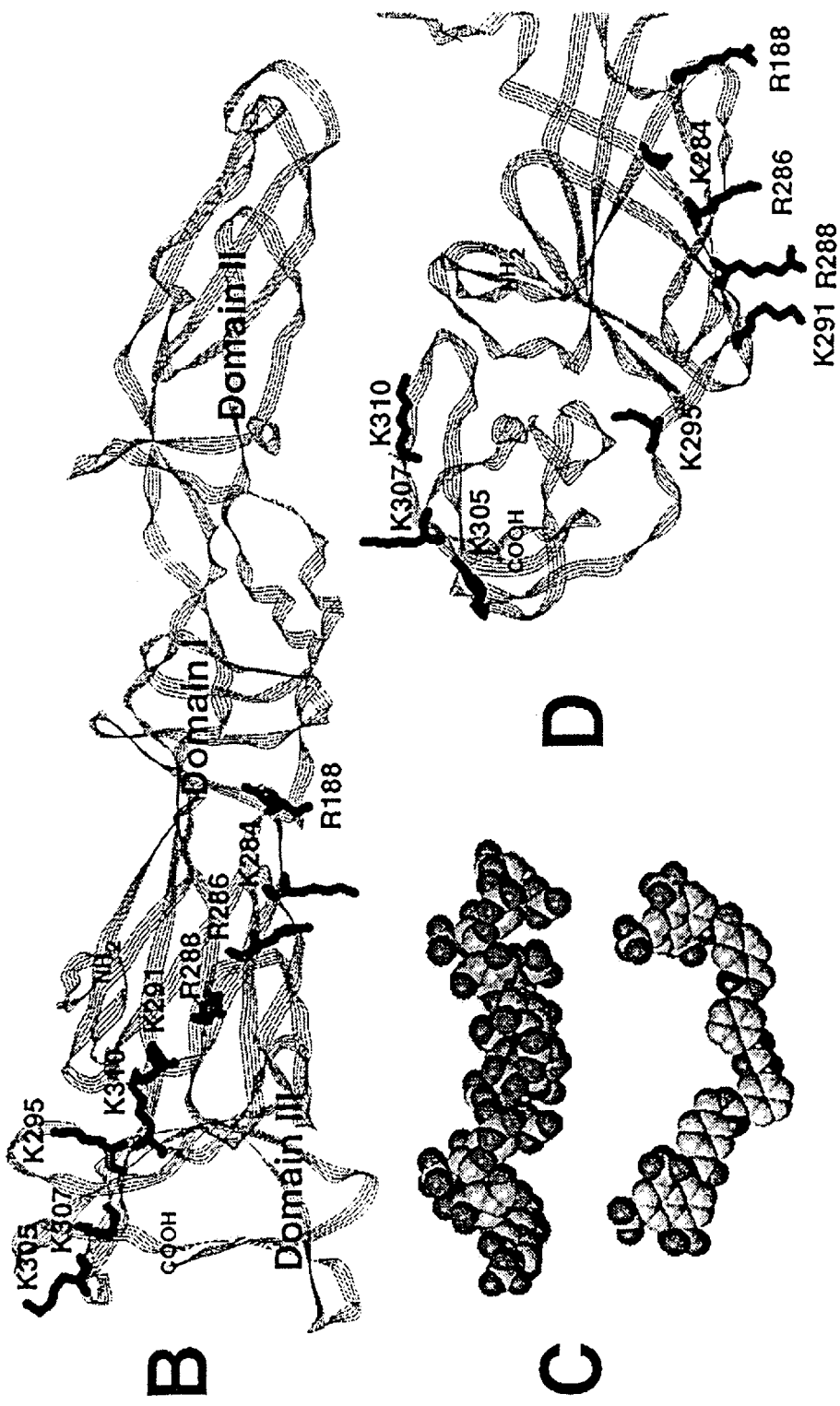

FIG. 4 illustrates proposed GAG-binding sites in envelope protein.

A) Primary sequences of the two predicted GAG-binding motifs in dengue virus envelope protein (single letter amino acid symbol); first motif (top SEQ ID NO:1), second motif (bottom SEQ ID NO:2). Predictions are based on an algorithm that searches for basic amino acid clusters separated by turns. Basic amino acids are represented by bold face lettering (K=lysine, R=arginine). Positions in the sequence are numbered at each end.

B) Predicted structure of the first GAG-binding motif in dengue virus envelope protein. The dengue virus envelope protein sequence was modeled on the x-ray crystal structure of TBE virus envelope protein, with which it shares 60% sequence homology. The envelope protein monomer is shown in ribbon form, displayed along its longitudinal axis, and as an external side view; the 3 structurally distinct domains are indicated. Within the first putative GAG-binding motif (positions 188, and 284–310) the basic amino acids form an extended positively charged domain that is externally exposed on the sides and end of domains I/III that is capable of accommodating a decasaccharide or Suramin molecule. The second GAG-binding motif (between amino acids 386–411), for which there is no structural information, is predicted to be situated in domain III close to the carboxy-end of the first binding motif. The basic amino acids are shown in solid black as stick figures, and are identified by number in sequence and single letter amino acid code.

C) Heparin decasaccharide (top) and Suramin (bottom) are structurally modeled based on x-ray crystallographic data of related sulfonated dyes, and a heparin hexasaccharide.

D) Alternate view of first GAG-binding motif. The region of interest from panel B is rotated 90° around its long axis to generate a view as if looking down on the virus and envelope protein. The first GAG-binding motif occurs in two distinct regions, the amino-end (positions 188, and 284–295) is on the side of domains I/III, and is capable of independently interacting with a decasaccharide or Suramin molecule. The carboxy-end (amino acids 305–310) occurs after a turn that places it on the end surface of domain III, possibly forming part of a joint binding region with the second GAG-binding motif. The basic amino acids are shown in solid black as stick figures, and are identified by number in sequence and single letter amino acid code.

Figure 5:
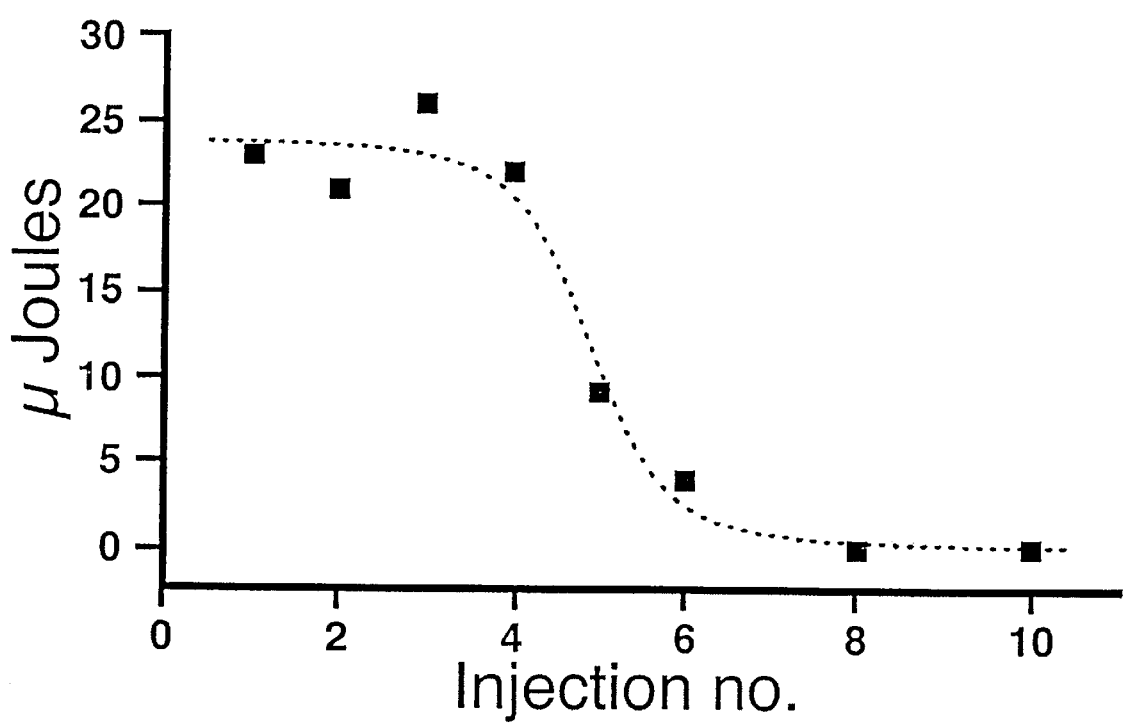

FIG. 5 shows isothermal titration calorimetry measurement of binding of whole heat-killed dengue virus to low molecular weight heparin. Dengue 2 Tonga strain virus was purified over a cesium chloride gradient, heat-killed, and diluted to an envelope protein concentration of 3 μM in 10 mM $N_2$ $PO_4$ buffer. Repeated aliquots of 50 μM low molecular weight heparin were added, and thermal data collected. Abscissa: Injection number. Ordinate: μ Joules heat released. Binding curves were generated by integrating the area of each peak detected. Curve fitting was modeled on a non-cooperative multivalent interaction.

Figure 6:
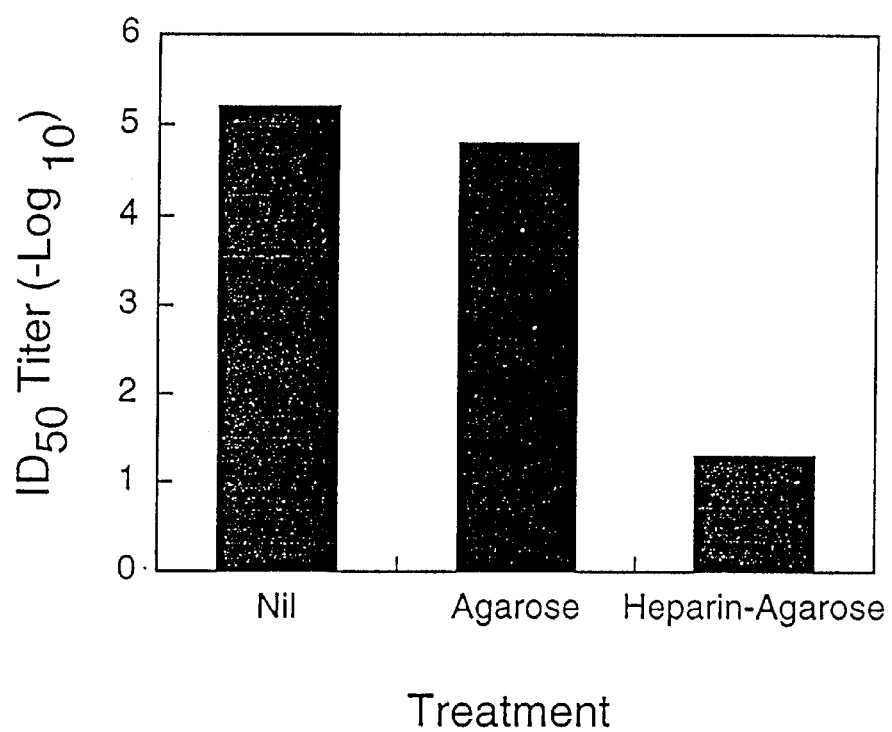

FIG. 6 shows binding of viable dengue virus to immobilized heparin, resulting in its removal from liquid suspension. A high titer stock of dengue 2 Tonga strain virus was passed over a column of heparin-agarose, and an identical viral stock was passed over a control column of unsubstituted agarose. Perfusates were collected and retitered in the infectivity assay as described for FIG. 3. Abscissa: virus samples applied to each column. Ordinate: $-\log_{10}ID_{50}$ titer.

Figure 7:
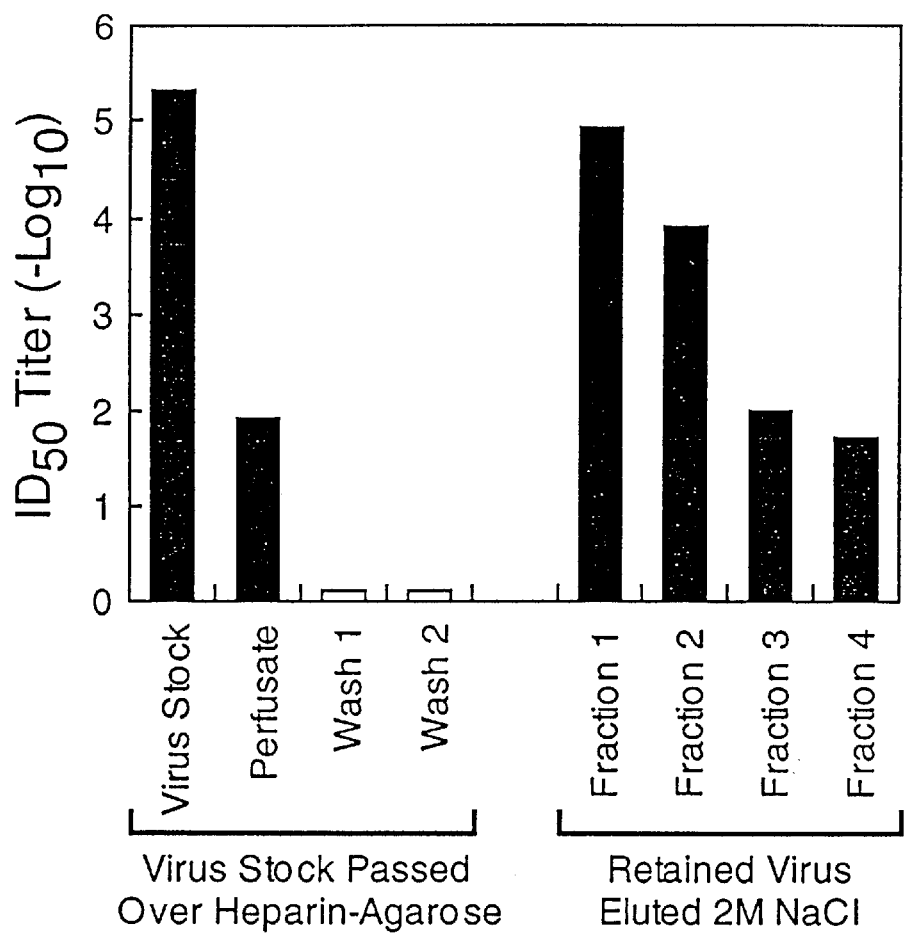

FIG. 7 demonstrates that viable dengue virus bound to immobilized heparin can be released for later analysis. A high titer stock of dengue 2 Tonga strain virus was passed over a column of heparin-agarose, and the column washed twice. Retained virus was eluted with 2M NaCl×4 fractions. Samples were tested in the infectivity assay, as described for FIG. 3. Abscissa: samples tested. Virus stock: before application to heparin-agarose column. Perfusate, samples collected after perfusion through column: Wash 1 and 2, samples collected after subsequent perfusion of column with saline. Fractions 1–4, samples collected after eluting the column with 4 sequential aliquots of 2M NaCl. Ordinate: $-\log_{10}ID_{50}$ titer of samples. The lower limit of sensitivity for the assay=1.5.

Figure 8:
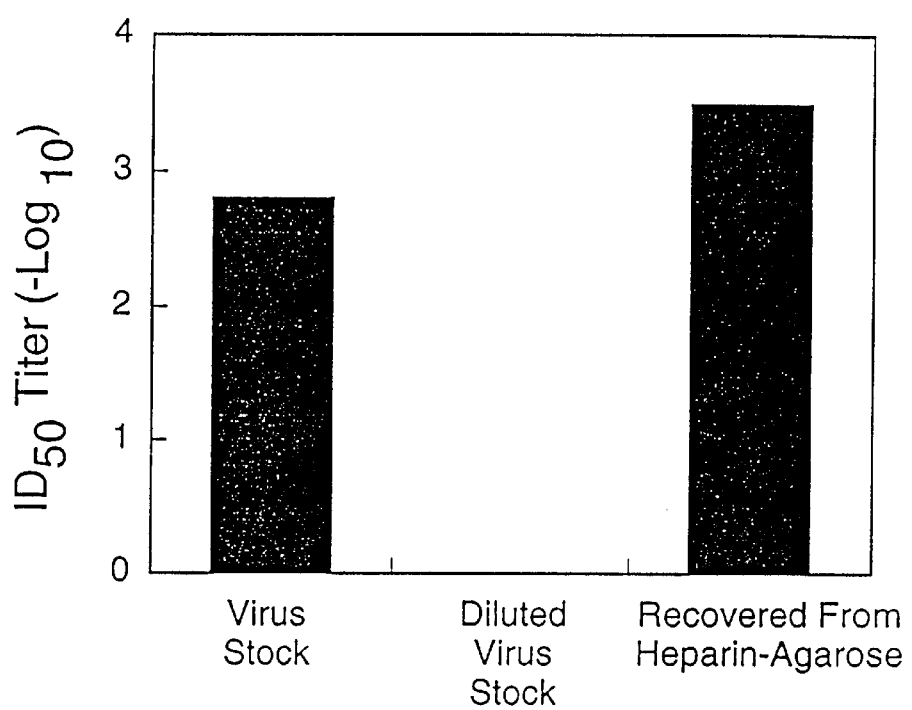

FIG. 8 shows viable virus heparin affinity chromatography used to concentrate dilute virus to a detectable concentration. A stock of dengue 2 Tonga strain virus was diluted to a level at which it could not be detected in the infectivity assay (titer<1.5 in 20 ml volume of culture medium). The dilute suspension was then perfused through a column of heparin-agarose, and the retained virus eluted in a 1 ml volume with 2M NaCl, and tested in the infectivity assay. Abscissa: samples. Virus stock: original virus stock preparation before dilution; Diluted virus stock, virus preparation diluted to 20 ml; Recovered from heparin-agarose, virus eluted from heparin-agarose column with 2M NaCl. Ordinate: $-\log_{10}ID_{50}$ titer of samples. The lower limit of sensitivity for the assay=1.5.

Figure 9:
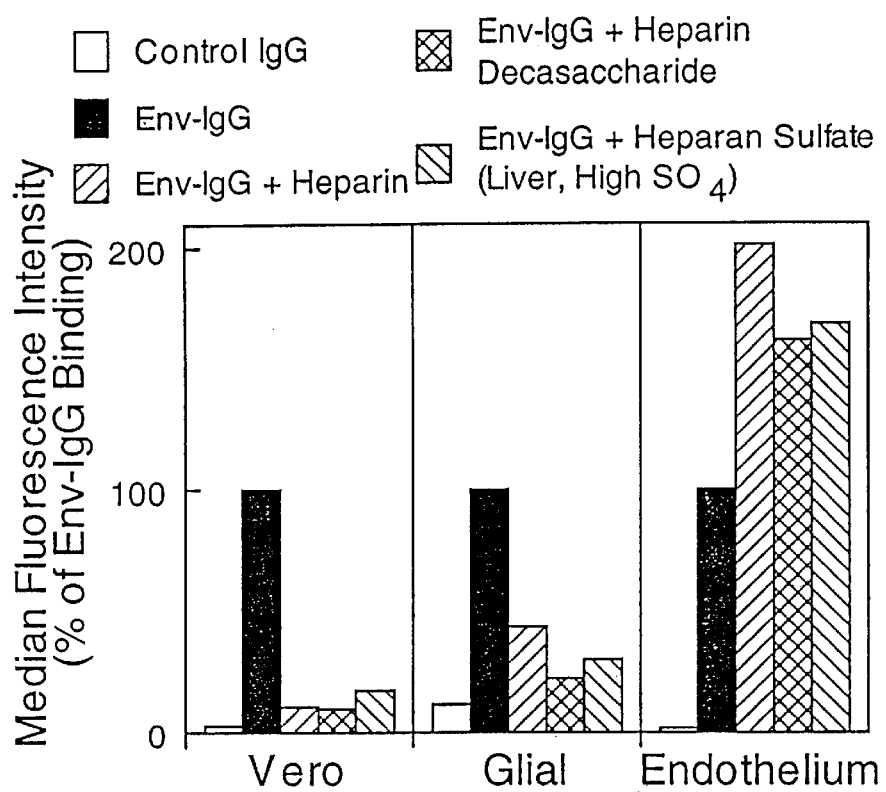

FIG. 9 illustrates that GAGs fail to inhibit envelope protein binding to endothelial cells. That there would be a single dengue virus envelope protein receptor common to all target cells was tested by using soluble GAGs as competitive antagonists of envelope protein binding to 3 cell types: Vero cells, glial cells, and human endothelial cells. Env-IgG was incubated with cells±heparin, heparin decasaccharide, or highly sulfated HS (all 10 μg/ml). Binding was quantitated by flow cytometry. Control IgG=non-specific binding. Abscissa: cell type. Ordinate: Median Fluorescence Intensity for each sample, expressed as a percentage of the binding of Env-IgG to each cell type.

Figure 10:
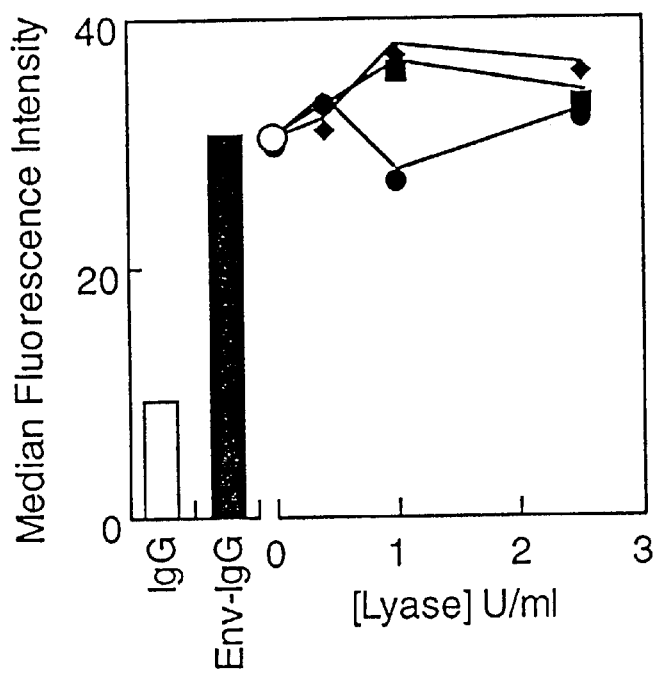

FIG. 10 shows that GAG-lyases fail to inhibit envelope protein binding to endothelial cells. To further test if GAGs were receptors for envelope protein on endothelial cells, endothelial cells were treated with specific GAG lyases, followed by assessment of envelope protein binding. The same protocol was used as described for FIG. 2A. Cells were incubated with Chondroitin ABC lyase (■■■), Heparin lyase I (●■●), and Heparin lyase III (◆■◆), 0.4–2.5 U/ml, and envelope protein binding assessed. Abscissa: binding of envelope protein to untreated cells is indicated by Env-IgG column. Background binding to untreated cells is indicated by IgG column. Envelope protein binding to mock digested cells (digestion buffer without enzyme) (O). Ordinate: Median Fluorescence Intensity for each sample.

Figure 11:
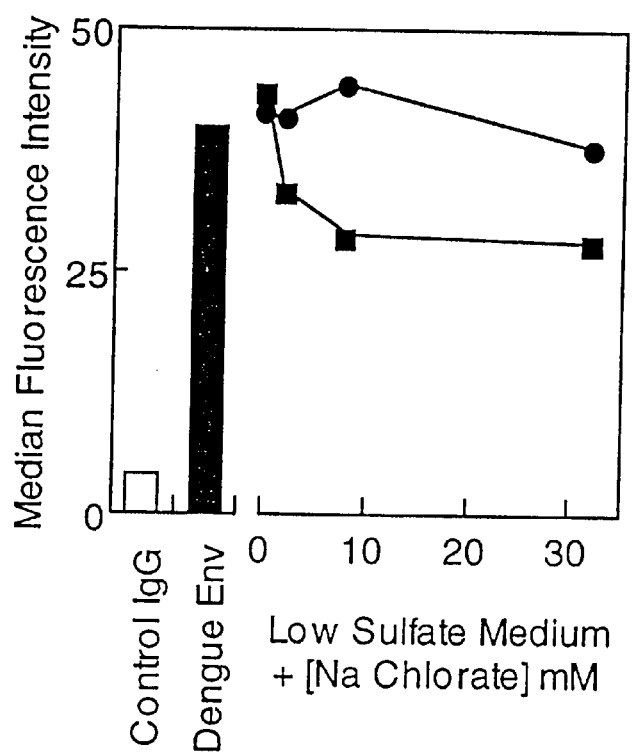

FIG. 11 illustrates that dengue virus endothelial cell receptor is partially sulfation-dependent. To test if the dengue virus receptor on endothelial cells shared the characteristic of sulfation-dependence with the dengue virus receptor on Vero cells, endothelial cell dependence on sulfation for envelope protein binding was tested. Human umbilical vein endothelial cells were assessed as described in FIG. 2C. Cells were cultured in normal medium or low-sulfate medium, in the presence of sodium chlorate (0–32 mM). Replicate cells were supplemented with 2 mM $Na_2SO_4$. Envelope protein binding was assessed after 48 hours. Abscissa: binding of envelope protein to cells in normal medium is indicated by Dengue Env. column. Background binding to cells in normal medium is indicated by Control IgG column. Cells incubated in low-sulfate medium and sodium chlorate (■■■). Cells incubated in low-sulfate medium and sodium chlorate and sodium sulfate (●■●). Ordinate: Median Fluorescence Intensity for each sample.

Figure 12:
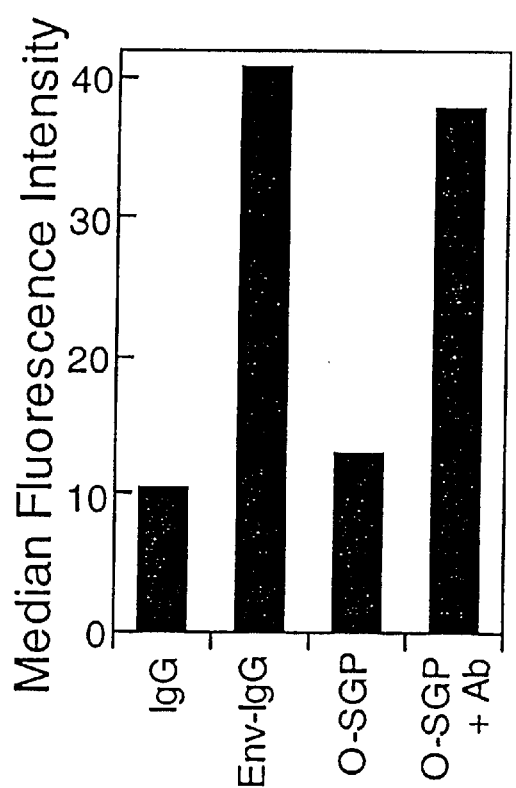

FIG. 12 shows that dengue virus endothelial cell receptor is sensitive to O-sialoglycopeptidase digestion, indicating it is a mucin. A subset of O-linked glycoproteins, restricted to sialylated or sulfated mucins, is defined by their unique susceptibility to digestion with the metalloprotease enzyme O-sialoglycopeptidase (O-SGP). The finding that the endothelial cell envelope protein receptor was partially sulfation-dependent, yet was not a GAG, suggested that it was a mucin, another type of sulfated complex glycoprotein. To test if the endothelial cell envelope protein receptor was a mucin, endothelial cells were incubated with O-SGP, followed by assessment of envelope protein binding. Envelope protein binding was assessed after endothelial cells were incubated with O-SGP (1/30 dilution of enzyme stock solution, for 1 hour at 37° C.). A specificity control consisted of co-incubating a neutralizing antibody to O-SGP (bovine serum, 1/10 dilution of antiserum stock) with the O-SGP and cells. Abscissa: cell treatments. Binding of envelope protein to untreated cells indicated by Env-IgG column. Background binding indicated by IgG column. O-SGP: enzyme incubated with cells prior to testing envelope protein binding. O-SGP+Ab: enzyme and enzyme-antiserum incubated with cells prior to testing envelope protein binding. Ordinate: Median Fluorescence Intensity for each sample.

Figure 13:
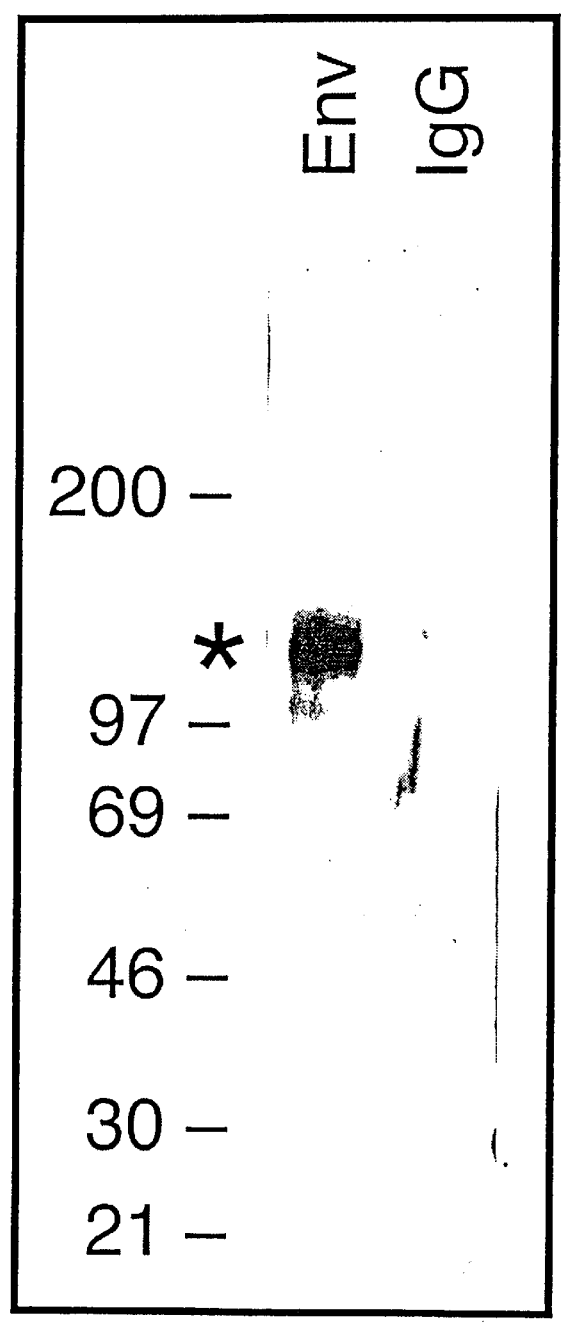

FIG. 13 illustrates that a dengue virus receptor on endothelial cells is a 135 kD cell-surface protein. To physically characterize the endothelial cell envelope protein receptor, recombinant envelope protein was used to affinity precipitate an endothelial cell lysate, followed by SDS-PAGE, and detection of precipitated protein by blotting. A monolayer of human umbilical vein endothelial cells was surface-biotinylated with NHC-LC-biotin (Pierce), lysed in 1% Triton X-100, and incubated with Env-IgG or control human IgG directionally immobilized on protein-A Sepharose beads. After washing, protein was eluted from the beads into sample buffer and resolved by 10% SDS-PAGE. Proteins were electrotransferred to nitrocellulose membrane, and detected by incubation with peroxidase-avidin, and enhanced chemiluminescence (Amersham). Lanes labeled with precipitating reagent, Env-IgG (Env) or control human IgG (IgG). Molecular Weight markers×$10^{-3}$ on left. 135,000 molecular weight precipitated protein band indicated by (*).

DESCRIPTION OF THE PREFERRED EMBODIMENT

Methods and compositions for the isolation, diagnosis and treatment of microorganisms such as flavivirus and hemorrhagic fever virus (HFV) infections are based on the polyanion-dependent interaction of microorganisms such as flaviviruses and HFV's as exemplified by dengue virus, with target cells. Compounds such as heparin, highly sulfated heparan sulfate and synthetic polyanions such as Suramin, inhibit interaction between the virus and target cells, thereby disrupting the infective process.

An endothelial cell receptor utilized by flavivirus and HFV envelope protein to bind to vascular endothelial cells is a sulfated O-linked mucin-like glycoprotein, a class of molecules related to, but distinct from, glycosaminoglycans (which includes the dengue virus receptor or other cell types such as Vero cells). To characterize the endothelial receptor, the procedures described in FIGS. 9–13 were used. Endothelium forms the inner lining of the entire cardiovascular system, and is likely a natural target for dengue virus and other HFVs; the pathophysiology of dengue virus infection is associated with a variety of vascular disturbances, and endothelial cells are readily infected by dengue virus.

Synthetic sulfated molecules were capable of blocking the binding of dengue virus envelope protein to both Vero and endothelial cells. One compound, Suramin, a practical pharmaceutical, (that is, known to be safe and efficacious for other uses) was a potent inhibitor of dengue virus infection of Vero cells, and completely prevented infection at high doses.

The region within the dengue virus envelope protein responsible for binding to target cells was identified. Initially, the target cell binding motif appeared to be expressed at the carboxy-terminus of the molecule. Examination of the dengue virus envelope protein sequence revealed two glycosaminoglycan-binding motifs at the carboxy-terminus; the first could be structurally modeled and formed an extended binding surface of basic amino acids, sufficiently large and accessible to interact with a glycosaminoglycan. Recombinant dengue virus envelope protein bound avidly to heparin, a close homologue of cellular heparan sulfate. Motif 1 extends between amino acids at positions 284–310 and has the sequence KCRLRM-DKLQLKGMSYSMCTGKFKIVK (SEQ ID NO:1; basic amino acids are shown in bold). Motif 2 extends from position 386–411 and has the sequence QLKLDWFKKGS-SIGQMFETTMRGAKR. As an initial approach (SEQ ID NO:2) to determining if binding to cellular GAGs/mucins is a common feature of other HFVs, the peptide sequences of 4 other HFVs were examined for GAG-binding domains. Domains were readily identified in Marburg virus (KKGPATTAPNTTNEHFTSPPPTPSSTAQHLVYFRRK RSILWR), (SEQ ID NO:3) Yellow Fever virus (KGTSYKICTDKMFFVK), (SEQ ID NO:4) Ebola virus (GGRRTRREAIVNAQPKC), and (SEQ ID NO:5) Lassa Fever virus (KSCPKPPHRLNHMGICSCGLYKQPGVPVKWKR) (SEQ ID NO:6).

That a) dengue virus envelope protein binds to heparan sulfate and related sulfated glycoproteins on target cells, b) this interaction is a critical determinant of infectivity, and c) a pharmaceutical compound prevents infection by interfering with this interaction, reveal avenues toward pharmacotherapy for flavivirus and HFV infection. This is of particular interest to countries in which flavivirus and HFV infections are a health problem.

Glycosaminoglycan-binding motifs in two small regions of the envelope protein sequence (including 27 and 26 amino acids each), indicated that these regions are critically involved in mediating infection. Development of antibodies to these regions is a strategy to prevent infection by blocking the binding of the virus to target cells, and thus these regions may form the basis for the development of a vaccine capable of protecting against all serotypes of dengue virus 1, 2, 3 and 4. As well as making antibodies to the GAG-binding motifs in the envelope protein as an approach to making a vaccine, another vaccine approach is to generate virus that has attenuated infectivity, by causing mutations in the GAG-binding motifs. Mutant virus are injected, do not cause disease because of their attenuated infectivity, and generates a protective immune response. Development of recombinant virus with site-directed mutations in the GAG-binding motif regions is a means to produce a virus with attenuated infectivity that could be used as the basis of a vaccine for generation of a protective immune response.

That whole dengue virus binds avidly to heparin and related compounds indicates that heparin immobilized on a solid phase is suitable as a means for isolating microorganisms with suitable receptors, and an aid for clinical diagnostic studies of flaviviruses and HFVs in general. Dengue virus is only one of many pathogenic flaviviridae and HFVs. Glycosaminoglycan binding motifs exist in the envelope proteins of all the flaviviridae and HFV examined. Because of these similarities and because all the flavivirus family members share a similar envelope protein structure, it is expected that these other viruses also utilize glycosaminoglycan binding motifs to bind to and infect target cells. Microorganisms such as bacteria, protozoa and other viruses that bind to polyanions such as GAGs are also suitable for the practice of the invention.

Many flaviviruses and hemorrhagic fever viruses share considerable similarities of nucleotide and peptide sequence, as well as sharing many pathologic features. This suggests that the mechanism used by these viruses to bind to target cells will also be similar. Mutation sites affecting virulence and infectivity have been defined for flaviviruses (those causing Japanese encephalitis, Louping ill, Murray Valley encephalitis, TBE, and yellow fever). Many mutations occur proximate to glycosaminoglycan (GAG)-binding motif sequences defined for dengue virus envelope protein, that are considered to account for target cell binding activity. Moreover, GAG-binding motifs were identified by direct examination of the protein sequences of members of all the three genera of flaviviridae; flaviviruses (dengue 1, 3, 4, Japanese encephalitis, kunjin, Murray Valley encephalitis, powassan, St. Louis encephalitis, tick-borne encephalitis, west nile, yellow fever), pestiviruses (border disease, bovine viral diarrhea, classical swine fever) and hepatitis c viruses (hepatitis c, gb-a, gb-b, gb-c), as well as in the hemorrhagic fever viruses Ebola, Marburg and Lassa fever viruses. Identification of the receptors used by these viruses to bind to and infect target cells is an important issue in understanding their pathogenesis. Identification of the vascular endothelial receptor utilized by these microorganisms is a particularly important issue as their widespread systemic dissemination and vascular pathology indicates vascular tropism and trafficking.

Thus, studies to develop pharmacotherapeutics and vaccine candidates for dengue virus are also applicable to other pathogenic microorganisms such as flaviviruses and HFVs. Isolation of virus from clinical specimens may fail in cases in which infection is later proven by detection of antibodies; this may be due to problems with the presence of undetectably low numbers of virus particles in clinical fluids such as blood. Immobilized heparin may be able to be used to concentrate virus for improved detection by culture, molecular, or immunologic detection techniques.

Vascular endothelium is an attractive target for gene therapy, however introduction of genetic material into endothelial cells is relatively inefficient. Demonstration that dengue virus envelope protein binds avidly to endothelial cells indicates that gene transfer agents that are constructed to express dengue virus envelope protein determinants may facilitate targeting to endothelial cells.

The following are aspects of the present invention:

i) The cellular receptor utilized by dengue virus to bind to and infect at least one target cell type, Vero cells, is an unusually highly sulfated form of the glycosaminoglycan heparan sulfate.

ii) Recombinant dengue virus envelope protein binds avidly to human vascular endothelial cells. The dengue virus envelope protein receptor for vascular endothelial cells is not a glycosaminoglycan, but is a related compound, a sulfated O-linked mucin-like glycoprotein.

iii) Synthetic compounds that mimic structural characteristics of sulfated polyanionic glycoproteins block binding of dengue virus envelope protein to target cells.

iv) One synthetic compound, Suramin, completely prevents infection of target cells by dengue virus. Suramin is a pharmaceutical compound suitable for human administration.

v) The dengue virus envelope protein binds to the glycosaminoglycan heparin (an analog of heparan sulfate). Examination of the dengue virus envelope protein sequence revealed two unusual glycosaminoglycan-binding motifs at the carboxy-terminus; the first could be structurally modeled and formed an unusual extended binding surface of basic amino acids, sufficiently large and accessible to interact with a glycosaminoglycan. These regions are suitable as the foci for development of reagents that specifically interfere with envelope protein binding and infectivity, and to generate an effective vaccine.

vi) Similar glycosaminoglycan-binding motifs were also identified in the envelope proteins of other members of the flavivirus family and in other hemorrhagic fever viruses. These viruses include pathogens causing disease in humans and animals that are of global health, agricultural, and economic significance. Examples include pathogens of major agricultural importance, such as pestiviruses, as well as of general medical significance such as the hepatitis C viruses. Investigation of these viruses could lead to the development of novel therapeutics and vaccine candidates.

EXAMPLE 1

Binding of Dengue Virus to Host Cells

Immunohistochemical examination of the binding of dengue virus envelope protein to cultured cells demonstrated binding to the extracellular matrix as well as to the cell surface, prompting examination of the role of GAGs as target cell receptors. Vero cells were used as targets because they are derived from a species susceptible to dengue virus infection, and suitable for infection in vitro by dengue and other viruses. Target cell binding experiments were performed with recombinant dengue virus envelope protein, and the biological relevance of results were confirmed by testing in infectivity assays.

Soluble GAGs were assessed for activity as competitive antagonists of envelope protein binding to Vero cells (FIG. 1A). Heparin had potent inhibitory activity (the dose for 50% inhibition [$ID_{50}$] was 0.3 µg/ml), while other GAGs and dextran sulfate, had no effect. The heparin-binding activity of the envelope protein was examined by incubating radiolabeled soluble envelope protein with immobilized heparin and eluting with NaCl (FIG. 1D). Envelope protein bound to heparin, and was eluted with 0.5 M NaCl, indicating a high affinity interaction with heparin in the low µM to high nM range. Heparin is not a constituent of cell membranes, but is a close structural homologue of heparan sulfate (HS), which is widely expressed on the surface of cells and in extracellular matrices. Thus, the failure of heparan sulfate to act as a competitive antagonist of envelope protein binding was unexpected, especially as standard heparan sulfate preparations disrupt target cell binding by other microorganisms. Recent investigations into the structure of HS derived from a variety of sources has revealed a high level of heterogeneity, expressed as differences in primary sequence such as iduronic acid content, and the pattern and level of sulfation. As heparin is generally more highly sulfated than HS, an unusually highly sulfated liver-derived HS (1.1 sulfates/disaccharide) was tested for activity in inhibiting envelope protein binding, and compared with a testis-derived HS with a lower degree of sulfation (0.6 sulfates/disaccharide) (FIG. 1B); only the highly sulfated HS significantly inhibited binding ($ID_{50}$ 4 µg/ml). Binding was completely prevented at high doses, suggesting that highly sulfated HS was able to mimic critical structural characteristics of the cellular receptor; it was however a less potent inhibitor than heparin. These data represent the first demonstration of functional differences between structurally distinct HS.

HS and heparin have a primary structure that consists of repeating disaccharide units. To determine the minimum sized structure required to occupy the envelope protein binding site, homogenous heparin-derived oligosaccharides ranging in size from di- to deca-saccharides, were tested for activity in inhibiting envelope protein binding to Vero cells (FIG. 1C). Only the fully sulfated heparin-derived decasaccharide had an inhibitory effect, and this was similar in potency to that of heparin ($ID_{50}$ 0.3 µg/ml). The failure of equivalent concentrations of smaller oligosaccharides, and a control decasaccharide containing the heparin-derived antithrombin III binding motif pentasaccharide to inhibit binding, provided compelling evidence that the inhibitory effect observed with HS and heparin is not simply a non-specific charge effect, but rather suggests a specific receptor-like interaction.

Experiments were next performed to demonstrate that the inhibitory effect of highly sulfated HS on envelope protein binding was due to competition with a similar molecular species on the target cell. Vero cells were treated with specific GAG lyases, followed by assessment of envelope protein binding (FIG. 2A). Heparin lyase I (degrades heparin and highly sulfated domains in HS), and heparin lyase III (specific for HS), both completely prevented envelope protein binding. Chondroitin ABC lyase (degrades chondroitin and dermatan sulfate) was ineffective. These data are consistent with an expectation that a highly sulfated HS is a cellular receptor for the dengue virus envelope protein. To further assess the role of cell surface GAGs as envelope protein receptors, binding of envelope protein to lines of mutant CHO cells with a range of defects in GAG synthesis and expression was measured (FIG. 2B). Envelope protein bound to wild type cells, but there was no binding to any of the mutant cell lines, including pgsD-677 which is deficient only in HS expression (and accumulates increased levels of other GAGs), providing further evidence that the envelope protein receptor is HS.

The result of comparing high and low sulfated forms of HS as inhibitors of envelope protein binding indicated that the degree of sulfation was functionally important. To determine if target cell sulfation is required for envelope protein binding, Vero cells were cultured in low-sulfate medium, treated with the specific sulfation inhibitor sodium chlorate, and the effects on envelope protein binding were assessed (FIG. 2C). Culture in low sulfate medium was sufficient to substantially inhibit envelope protein binding, and the addition of sodium chlorate led to complete loss of binding. The specificity of this effect was confirmed by supplementing the sulfate-deprived and chlorate-treated cells with an excess of sodium sulfate, and demonstrating recovery of envelope protein binding. This does not mean that all inhibitors suitable to inhibit cell-microorganism binding must be sulfated, but if not, a comparable chemical structure must be present.

To examine the contribution to infectivity of the viral envelope protein interaction with target cell GAGs, it was determined whether soluble GAGs could competitively inhibit infection of Vero cells by dengue virus. Heparin, and the high and low sulfated forms of HS were co-incubated with dengue virus, added to Vero cells, and the cells observed for infection (FIG. 3A). Results obtained paralleled those obtained with the recombinant envelope protein. Both heparin and the highly sulfated form of HS substantially inhibited infection (79 and 7.9 fold inhibition respectively at the highest doses used), while the low-sulfated form of HS had no significant effect (2 fold inhibition). These data indicate that the results obtained with the recombinant envelope protein are an accurate representation of the interaction of dengue virus with target cells, that the interaction of viral envelope protein with target cells is a critical determinant of infectivity, and that inhibition of that interaction prevents infection of a highly susceptible cell type.

The demonstration that a heparin-derived oligosaccharide was an effective inhibitor of envelope protein binding suggested that other polyanionic molecules might also prevent target cell binding and infectivity. Several polyanionic compounds were tested; sulfated lactobionic acid, the non-anticoagulant heparin Astenose, and the polysulfonate pharmaceutical Suramin inhibited envelope protein binding. These compounds were further tested for activity in preventing dengue virus infection of Vero cells. Suramin was found to prevent infection, and was completely protective at high doses, reducing infection to below the assay detection limit (FIG. 3B). In subsequent experiments the effect of Suramin was shown, as expected, to be on virus and not target cells. Incubation of Vero cells with Suramin, followed by washing before exposure to virus, had no effect on infectious titer; incubation of virus with Suramin was necessary to prevent infection.

EXAMPLE 2

GAG-Binding Motifs in Dengue Virus

Previous work on binding interactions between glycosaminoglycans and proteins suggested the importance of contiguous clusters of basic amino acids within the protein primary structure in binding to heparin, with charge-interactions thought to be of primary importance. However, this represents only one of a number of protein motifs that bind GAGs. Recent studies indicated that GAG binding can also be predicted by defining multiple regions enriched for basic amino acids, separated by turns that bring these basic regions into apposition. Examination of the envelope protein sequence of the dengue 2 Tonga strain virus, revealed two such GAG-binding motifs, between amino acids at positions 284–310, and 386–411; the primary sequences are shown in FIG. 4A.

The crystallographic structure of a fragment of the envelope protein of another flavivirus, tick-borne encephalitis (TBE) virus, was recently determined. All flavivirus envelope proteins are highly homologous, including the complete conservation of 12 cysteines, allowing the dengue virus envelope protein structure to be modeled based on that of TBE (FIG. 4B). Flavivirus envelope proteins occur as elongated dimers lying flattened over the viral surface, and are folded into three distinct domains. Domain I forms a central β-barrel, and is generated from both amino- and carboxy-terminal sequences. Domain II forms an elongated finger-like structure that is likely to incorporate the motifs responsible for dimerization and membrane fusion. Domain III is generated from carboxy-terminal sequences, and is in the form of an immunoglobulin-like (IgC) module. A partial length dengue envelope protein construct incorporating sequences from the carboxy end of domain I and domain III (amino acid positions 281–283) had potent target-cell binding activity, while a construct incorporating the amino-terminal sequence was inactive, indicating that the carboxy-terminus structure contains the motifs responsible for virus binding to target-cells.

Examination of the position of the first GAG-binding motif indicates that it is externally exposed, commencing in domain I, and continuing into domain III (FIG. 4B). Six basic amino acids form an extended binding surface on the external side of domain I (viewed along the longitudinal axis). Five of these amino acids are derived from the amino-end of the first motif and occur between positions 284–295, the sixth is at position 188. Notably, this region is sufficiently large and accessible to interact with a decasaccharide or Suramin molecule (FIG. 4C). Three additional basic amino acids comprise the carboxy-end of the first GAG-binding motif (between 305–310). These are located after a turn that places this region on the upper end surface of domain III, viewed relative to the longitudinal axis (FIG. 4D). It is unclear whether a single heparin decasaccharide or Suramin molecule would have sufficient flexibility to simultaneously interact with both regions of the first GAG-binding motif (side surface of domain I, end surface of domain III). The carboxy-end of the first GAG-binding motif is conspicuous for its projection away from the virion surface, where it may be optimally situated for interaction with a target cell receptor.

The second GAG-binding motif (FIG. 4A) occurs in the region for which there is no structural data. However, the immediately preceding sequence is located on the end of domain III, and it is likely that the second GAG-binding motif is externally exposed in the same region. The GAG-binding motif might form a component of a receptor binding site in conjunction with the carboxy-end of the first GAG-binding motif. Chou-Fasman analysis of the second GAG-binding motif predicts a strand-turn-strand-turn-strand secondary structure, with basic amino acids in the strands brought into tightly clustered apposition by the turns, similar to that observed in the basic fibroblast growth factor GAG-binding motif.

Immunoglobulin-like folds are commonly associated with structures that have an adhesive function. The finding that domain III had this form, and that it extended perpendicular to the surface of the virus with a tip projecting further from the virion surface than any other part of the envelope protein, led Rey et al. (1995) to hypothesize that this region accounted for TBE virus receptor binding. Localization of target cell binding activity of dengue virus envelope protein to this region, definition of two GAG-binding motifs within externally accessible regions of domains I and III or the envelope protein, and demonstration that the envelope protein binds heparin and interacts with HS on target cells is consistent with this expectation and which is mediated by an interaction based on the GAG-binding motifs.

Studies of viral escape mutants have been widely used to identify regions in viral ectodomain proteins that are important targets of infection-neutralizing antibodies. Viruses that escape the inhibitory effect of antibodies and cause infection of target cells are recovered, and the sequence change responsible for epitope loss is determined. Eleven escape mutation sites have been defined for dengue 2 New Guinea C strain virus; four (36%) occur within the predicted GAG-binding motifs which correspond to just 11% of the envelope protein sequence. Spontaneous mutation of a dengue 2 Mexican strain virus within the second predicted GAG-binding motif at position 390 (Asp to Asn) was associated with attenuation of virulence, while mutation at the same position to the basic amino acid histidine increased virulence. Concentration of escape mutation and virulence-affecting sites within these restricted regions of the envelope protein indicates their critical significance to infectivity. Further, the ability of antibodies to bind to these regions of the native envelope protein confirms the prediction made from the structural model that they are externally exposed and available for receptor binding.

EXAMPLE 3

Dengue virus envelope protein binds to heparin

Identification of the dengue virus envelope protein receptor on Vero cells as a heparan sulfate indicated that the envelope protein should have heparin-binding activity. This was directly examined by incubating radiolabeled envelope protein with immobilized heparin, and eluting with NaCl. Envelope protein bound to heparin, and was eluted with 0.5 M NaCl, indicating a high affinity interaction. (See FIG. 1D).

EXAMPLE 4

Dengue virus envelope protein and whole virus have heparin-binding activity

Previous data (see FIG. 1D) indicated that dengue virus envelope protein underwent avid binding to immobilized heparin. The possibility that an interaction of whole dengue virus with heparin could also be demonstrated was tested by using the technique of isothermal microtitration calorimetry; whole heat-killed dengue virus was mixed with increasing concentrations of low molecular weight heparin, and the heat generated measured as an index of the interaction. This demonstrated a dissociation constant of approximately 15 nM for the binding of dengue virus to heparin. (See FIG. 5).

EXAMPLE 5

Viable dengue virus specifically interacts with heparin immobilized on an agarose support An experiment was performed to assess if viable dengue virus would also interact with immobilized heparin, and to determine if this interaction could be exploited to remove dengue virus from a suspension. FIG. 6. relates the following: A high titer stock of dengue virus ($-\log_{10}$ ID$_{50}$ titer 5.2) was passed over a column of heparin-agarose, and an identical viral stock was passed over a control column of unsubstituted agarose to determine the specificity of the interaction. The perfusate was collected and re-titered. There was no significant reduction in titer after perfusion through unsubstituted agarose. However there was a reduction in titer to 1.3 (8000 fold reduction) after perfusion through heparin-agarose. This indicates that the avidity of the interaction with heparin was strong enough to immobilize virus under conditions of flow, and that it was capable of quantitatively removing viable virus from a high titer suspension.

EXAMPLE 6

Binding of dengue virus to heparin-agarose and recovery by elution with high-salt buffer An experiment was performed to confirm the results from the experiment demonstrated in FIG. 6, and to determine if viable virus could be recovered from immobilized heparin. As the experiment shown in FIG. 1D demonstrated that recombinant envelope protein could be eluted from immobilized heparin with a concentration of NaCl$\geq$0.5M, the heparin agarose column was perfused with 2M NaCl to release bound virus. As shown in FIG. 7, a high titer stock of dengue virus was passed through heparin-agarose, and the column washed ×2 with buffer. Retained virus was eluted with 2M NaCl ×4 fractions. All samples were then tested in the infectivity assay. (See FIG. 7) Perfusion through the column reduced the $-\log_{10}$ ID$_{50}$ titer from 5.3 to 1.9, with no virus detected in subsequent column washings (titer<1.5). 99.6% of the virus stock applied was retained on the column. Virus was however detected in the 2M NaCl eluate; 44% of the virus added to the column was recovered in the 4 fractions. These data not only indicate the significant avidity of the interaction between dengue virus and heparin, but also suggest clinical diagnostic potential for this approach to removing, recovering and concentrating dengue virus, and other heparin-binding viruses.

EXAMPLE 7

Recovery and concentration of dengue virus from an undetectable titer suspension A clinical application of viable virus heparin affinity chromatography is to recover virus from a suspension in which it was present at a titer too low to detect by current technology, and concentrate it to a level at which it can be detected. To assess the feasibility of this approach, a suspension of dengue virus (original titer 2.8) was diluted to a level at which it could not be detected in the infectivity assay (titer$\leq$1.5 in 20 ml volume of culture medium). The dilute suspension was then perfused through a column of heparin-agarose, and the retained virus eluted with 2M NaCl in a 1 ml volume, and tested in the infectivity assay. FIG. 8 shows perfusion of the undetectably low-titer viral stock through the heparin-agarose column led to quantitative retention and recovery of the virus applied. Virus was concentrated 1000 fold, and recovered at a level 100 fold above the minimum detection limit for the assay.

EXAMPLE 8

GAGs fail to inhibit envelope protein binding to endothelial cells

To test if a single dengue virus envelope protein receptor was common to all target cells, soluble GAGs were tested as competitive antagonists of envelope protein binding to 3 cell types: Vero cells, glial cells, and human endothelial cells (See FIG. 9). Heparin, heparin decasaccharide, and highly sulfated HS inhibited envelope protein binding to Vero and glial cells, consistent with the receptor on these cells being a HS. However, envelope protein binding to endothelial cells were increased by these compounds. This finding was confirmed in additional experiments including heparin concentrations up to 100 μg/ml.

EXAMPLE 9

GAG lyases fail to inhibit envelope protein binding to endothelium

To further test if GAGs were receptors for envelope protein on endothelial cells, endothelial cells were treated with specific GAG lyases, followed by assessment of envelope protein binding (see FIG. 10). The same protocol was used as described in FIG. 2A. None of the lyases, including the heparin lyases that completely abolished envelope protein binding to Vero cells, had any effect on binding to endothelial cells. These data confirm that the envelope protein receptor on endothelial cells is not a GAG, but is instead a related molecule, a sulfated mucin-like O-linked glycoprotein. As endothelial cells are likely to be a critical target cells for dengue infection in vivo, and as much of the pathology of dengue infection can be attributed to vascular involvement, the endothelial cell envelope protein receptor is important to identify.

EXAMPLE 10

Endothelial cell receptor for envelope protein is partially sulfation-dependent

The GAG envelope protein receptor on Vero cells was functionally sulfation-dependent. As glycoproteins other than GAGs may also functionally depend on sulfation, endothelial cell dependence on sulfation for envelope protein binding was determined (See FIG. 11). Cells were assessed as described in FIG. 2C. Culture in low sulfate medium alone was not sufficient to inhibit envelope protein binding; however, the addition of sodium chlorate led to a dose dependent partial inhibition of binding. The specificity of this effect was confirmed by supplementing the sulfate-deprived and chlorate-treated cells with an excess of sodium sulfate, and demonstrating complete recovery of envelope protein binding. Although the effect on endothelial cells was less than that observed with Vero cells, the chlorate dose-responsiveness, and the reversal with sodium sulfate both indicate that the effect was significant.

EXAMPLE 11

Envelope protein receptor on endothelial cells is a mucin

A subset of O-linked glycoproteins, restricted to sialylated or sulfated mucins, is defined by their unique susceptibility to digestion with the metalloprotease enzyme O-sialoglycopeptidase (O-SGP). The finding that the endothelial cell envelope protein receptor was partially sulfation-dependent, yet was not a GAG, suggested the possibility that it was a mucin, another type of sulfated complex glycoprotein. To test if the endothelial cell envelope protein receptor was a mucin, endothelial cells were incubated with O-SGP, followed by assessment of envelope protein binding, FIG. 12. O-SGP abrogated binding, consistent with the envelope protein receptor on endothelial cells being a mucin. A specificity control consisting of neutralizing antibody to O-SGP completely blocked the inhibitory effect of enzyme. Control serum had no effect. The effect of O-SGP was reproducible and dose-dependent.

EXAMPLE 12

Endothelial cell receptor for envelope protein is a 135,000 dalton molecular weight cell-surface protein To physically characterize the endothelial cell envelope protein receptor, recombinant envelope protein was used to affinity precipitate an endothelial cell lysate, followed by gel electrophoresis, and detection of precipitated protein by blotting (see FIG. 13). A relevant envelope protein endothelial receptor must be expressed on the apical (lumenal) cell surface; to ensure that any protein detected was apically exposed, a confluent monolayer of human umbilical vein endothelial cells was first surface-biotinylated with cell-impermeant NHC-LC-biotin (Pierce), lysed in 1% Triton X-100, and incubated with Env-IgG or control human IgG directionally immobilized on protein-A Sepharose beads. After washing, protein was eluted from the beads into sample buffer and resolved by 10% SDS-PAGE. Proteins were electrotransferred to nitrocellulose membrane, and detected by incubation with peroxidase-avidin, and enhanced chemiluminescence (Amersham). Env-IgG specifically precipitated a single major endothelial cell surface molecule, having an estimated molecular weight of 135,000 daltons.

MATERIALS AND METHOD

Recombinant Envelope Protein cDNA Construct

The dengue 2 virus envelope protein cDNA (Genbank accession X54319 was obtained as a plasmid clone pTZD2E4 from Dr. Maguire (Univ. Otago, New Zealand). The region encoding the envelope protein, extending from the start codon to the beginning of the transmembrane region (nucleotides 1 to 1272), was subcloned using PCR amplification. Additional nucleotides were included in the sense strand oligonucleotide to generate an upstream Nhe I restriction site. The sense strand oligonucleotide primer sequence was (Nhe I site underlined) 5'-CTA GCT AGC GAT GCG CTG CAT AGG AAT ATC AAA TAG GGA-3'. (SEQ ID NO:7) Two oligonucleotide primers for the antisense strand were utilized sequentially for PCR, in order to add sequence to the downstream region, encoding an in-frame duplex heart muscle kinase target site (HMK, single amino acid code RRASVGRRASV (SEQ ID NO:8), followed by a Bgl II restriction site. The first antisense strand oligonucleotide primer had the sequence (HMK target site underlined) 5'-ACC TAC AGA TGC ACG TCG AGA TCC AAA ATC CCA GGC TGT-3'. (SEQ ID NO:9) PCR was initially performed with the sense strand oligonucleotide and the first antisense strand oligonucleotide. The product was recovered and used as the template for a second round of PCR, using the same sense strand oligonucleotide, and the second antisense strand oligonucleotide sequence (HMK target site underlined, Bgl II site italicized) 5'-CGG AAG ATC TAC TGA TGC ACG ACG ACC TAC AGA TGC ACG TCG-3'. (SEQ ID NO:10) The final PCR product was digested with Nhe I and Bgl II.

The plasmid utilized for expression was based on pcDNA3 (Invitrogen, San Diego, Calif.), a vector designed for eukaryotic expression. pcDNA3 was modified by ligating the cDNA for the signal peptide of CD5, and part of the heavy chain constant region of human IgG$_1$ into the plasmid multiple cloning site. The CD5 signal peptide was incorporated to facilitate secretion, the IgG domains were incorporated to facilitate purification and detection of expressed protein, and the HMK domains were introduced to facilitate radiolabeling by phosphorylation with $^{32}$P. Large scale plasmid preparations were purified by Qiagen anion-exchange chromatography.

Expression And Purification Of Envelope Protein

Plasmid constructs were transfected into COS-7 cells (American Type Culture Collection [ATCC, Rockville, Md.] CRL-1651) by calcium phosphate co-precipitation, and cultured post-transfection in Dulbecco's Modified Eagle Medium (DMEM) containing 2% fetal bovine serum (FBS), penicillin 100 U/ml, and streptomycin 100 µg/ml (all from Life Technologies Gibco BRL, Gaithersburg, Md.). Cell lysates were harvested after 96 hours. Cells from each 10 cm diameter dish were scraped into 0.75 ml cation free phosphate buffered saline (Gibco) containing 0.5% Triton X-100 (PBS-T) and protease inhibitors (leupeptin, aprotinin, soybean trypsin inhibitor, and pepstatin [all 1 µg/ml], and phenylmethylsulfonylfluoride [1 mM], all from Sigma, St. Louis, Mo.), sonicated for 1 min., and clarified by centrifugation at 14,000 g, 30 min., 4° C.

Recombinant protein was purified by affinity chromatography over protein A, utilizing its high avidity interaction with the Fc region of IgG. Protein A Sepharose (Zymed, San Francisco, Calif.) was incubated with 100 ml of cell lysate on a rotating platform overnight at 4° C., packed into a column, and non-bound protein was removed by washing the column with 10 bed volumes of PBS-T, and then 10 bed volumes of PBS without detergent. Bound protein was eluted in 4 bed volumes of Actisep elution medium (Sterogene, Carlsbad, Calif.), and dialyzed against 3 changes of PBS.

Envelope Protein Binding Assay

Vero cells were detached from their culture surface without proteases (incubated in cation-free phosphate buffered saline (PBS, Gibco-BRL) with 5 mM EDTA, 10 min. 37° C., washed, and incubated with envelope protein (10 µg/ml) and competitive antagonists (10 µg/ml unless otherwise indicated) in cation containing PBS with 1% normal goat serum (Gibco-BRL), for 1 hour at 4° C. Cells were washed two times, incubated with R-phycoerythrin labeled Fab$_2$ fragment of affinity purified goat antibody to human IgG Fc (5 µg/ml, Jackson Labs.) for 1 hour at 4° C., and washed two times. Cellular fluorescence and forward angle light scatter were quantitated by flow cytometry (FACScan, Becton Dickinson). A minimum of 10,000 cells was assessed from each treatment group. Data were accumulated only for viable cells; non-viable cells were excluded from analysis on the basis of low forward angle light scatter. Results were expressed as frequency histograms of fluorescence per cell. A value for median fluorescence intensity was derived from the fluorescence frequency histograms for each sample, and used to compare fluorescence between samples. In each experiment, controls consisted of untreated cells, cells incubated with only the secondary fluorochrome-labeled antibody, and cells incubated with normal human IgG followed by the secondary fluorochrome-labeled antibody.

Chondroitin sulfate (CS) from bovine trachea, dermatan sulfate (DS) from bovine mucosa, heparan sulfate (HS) from bovine kidney, heparin from bovine lung, keratan sulfate (KS) from bovine cornea, and dextran sulfate (DexS) (MW 5×10⁵) were obtained from Sigma Chemical Co. and used at a concentration of 10 µg/ml. In other experiments no inhibitory effect was observed with concentrations of CS, DS, HS, KS and DexS up to 30 µg/ml. HS (up to 30 µg/ml, bovine kidney) from Seikagaku Inc. also failed to inhibit envelope protein binding.

Envelope Protein Radio Labeling And Binding To Heparin

Recombinant envelope protein was engineered to express a phosphokinase target site immediately carboxy-terminal to envelope protein sequence to facilitate radiolabeling with $^{32}$P (Chen et al. 1996). 100 ng of envelope protein was incubated in a total volume of 30 µl buffer (20 mM Tris. HCl pH 7.4, 100 mM NaCl, 12 mM MgCl$_2$), with 5 U of cAMP dependent protein kinase catalytic subunit (Promega) and 1 mCi [γ-$^{32}$P] ATP (DuPont New England Nuclear), for 15 minutes at 37° C. Unincorporated $^{32}$P was removed by column chromatography (ProbeQuant, Pharmacia). Specific activity was consistently found to be >2×10$^8$ cpm/µg protein.

$10^6$ cpm of $^{32}$P-envelope protein in Na phosphate buffer (10 mM, pH 7.5) was added to 200 µl of immobilized heparin beads (Emphase-heparin, gift of Minnesota Mining & Manufacturing Co.), loaded into a column, and washed with loading buffer until eluted cpm was at background levels. The column was then perfused with increasing concentrations of NaCl in loading buffer (step-gradient, 100 mM, 250 mM, 500 mM, 1 M, 2 M) Twelve serial fractions were collected at each NaCl concentration.

Treatment of Cells with GAG Lyases

Cells were removed from their culture surface without proteases, and resuspended in 10 mM phosphate buffer pH 7.4, with 0.14 M NaCl, 3 mM KCl, 0.5 mM MgCl$_2$, 1 mM CaCl$_2$, 0.1% glucose, 1% fetal bovine serum (Gibco-BRL), and 0.5% bovine serum albumin (Sigma). GAG lyases chondroitin ABC lyase (EC 4.2.2.4), Heparinase I (EC 4.2.2.7), Heparinase III (EC 4.2.2.8), all from Sigma, were added to the cells and incubated at 37° C. for 1 hour. Replicate experiments with Heparinase (EC 4.2.2.7) & Heparan sulfate lyase (EC 4.2.2.8) obtained from Seikagaku Inc. had identical effects on subsequent binding of envelope protein.

Envelope Protein Binding to Mutant CHO Cells

For comparison of results between the different CHO cell lines, background median fluorescence intensity (cells incubated only with fluorochrome labeled antibody) was subtracted from the fluorescence obtained after incubation with envelope protein or control IgG, and the results expressed as a percent of the fluorescence obtained after incubating parent CHO-K1 cells with envelope protein.

Low-Sulfate Culture Medium For Testing Sulfation-Dependency Of Envelope Protein Binding To Cells Low sulfate Dulbecco's MEM free of cysteine and methionine was obtained from Gibco-BRL, and supplemented with methionine 1.5 µg/ml, cysteine 2.4 µg/ml, and 5% dialysed fetal bovine serum.

Infectivity Assay

Ten-fold serial dilutions, from $10^{-1}$ to $10^{-7}$, of a stock of freshly prepared dengue 2 New Guinea C strain virus was prepared, incubated with test compounds for 5 min at 4° C., and then added to Vero cells (500 cells/well in 96 well plates) for 5 min at 4° C. Non-bound virus was removed by washing ×3. The cells were cultured and observed for cytopathic effect, daily, for 7 days. Dengue virus infection was confirmed as the cause of cytopathic effect in selected wells by immunofluorescence analysis using a dengue type 2 specific monoclonal antibody. 16 wells were assessed for each experimental condition. The mean infectious titers were derived by cumulative averaging (Reed and Muench, 1938).

Screening Assay For Molecular Structures That Inhibit Binding Of Polyanion Microorganisms To Target Cell Receptors A screening assay for candidate molecular structures that inhibit binding of polyanion microorganisms to target cell receptors is an aspect of the invention. The assay comprises growing target cells adherent to the wells in 96-well tissue culture dishes. The wells are washed, and envelope protein derived from a microorganism whose envelope protein exhibits GAG-binding activity, is added to the cultured cells diluted in a physiological buffer solution, and incubated until binding to target cell receptors has reached a maximum level. Unbound envelope protein is removed by multiple washing of the wells with physiological buffer solution, and the level of binding is quantitated. Binding can be quantitated by either directly labeling the envelope protein with a radioisotope before it is added to the test wells, followed by measuring residual radioactivity in the wells, or by directly labeling the envelope protein with a fluorescent compound before it is added to the test wells, followed by measuring residual fluorescence in the wells.

An alternative approach to detection is to follow the incubation of unlabeled envelope protein in the test wells with a secondary detection reagent that consists of a radiolabeled or fluorescent-labeled reagent such as an antibody that was capable of specifically detecting bound envelope protein. Test compounds for screening are added to the cells with the envelope protein, and compounds that had activity as inhibitors of envelope protein binding are indicated by their activity in reducing the amount of envelope protein binding detected in this assay.

Documents Cited

Chen (1996) *J. Virology* 70:8765–8772.

Reed, L. J. and Muench, H. (1938) *Amer., J. Hygiene* 27:493–497.

Rey, F. A. et al. (1995) *Nature* 375:291–298.

What is claimed is:

1. A method for detecting a polyanion-binding microorganism in a biological sample, said method comprising:
   a) contacting the biological sample with an immobilized polyanion to which the microorganism from said biological sample adheres to form a polyanion-microorganism complex while the remainder of the biological sample is non-adherent to said polyanion;
   b) analyzing the complex to determine whether the microorganism is present; and
   c) releasing intact microorganism from said complex.

2. The method of claim 1, wherein the microorganism is a virus.

3. The method of claim 2, wherein the virus is a hemorrhagic fever virus.

4. The method of claim 2, wherein the virus is Hepatitis C.

5. The method of claim 2, wherein the virus is a flavivirus.

6. The method of claim 5, wherein the virus is a dengue virus.

7. The method of claim 6, wherein the dengue virus binds the polyanion through a polyanion binding motif having the sequence of SEQ ID NO:1.

8. The method of claim 6, wherein the dengue virus binds the polyanion through a polyanion binding motif having the sequence of SEQ ID NO:2.

9. The method of claim 1, wherein the polyanion is selected from the group consisting of heparin, highly sulfated heparan sulfate, a synthetic polyanion, and a dengue virus envelope protein receptor derived from Vero cell glycosaminoglycan (GAG) or endothelial mucin or analogues thereof.

10. The method of claim 1, wherein said immobilized polyanion is a sulfated heparin-derived decasaccharide.

* * * * *

UNITED STATES PATENT AND TRADEMARK OFFICE
CERTIFICATE OF CORRECTION

PATENT NO.   : 6,197,568 B1
DATED        : March 6, 2001
INVENTOR(S)  : Rory M. Marks et al.

It is certified that error appears in the above-identified patent and that said Letters Patent is hereby corrected as shown below:

Title page,
Item [73], insert -- ; The Health Research Council of New Zealand, Auckland, New Zealand; The University of Iowa Research Foundation, Iowa City, Iowa -- after "(US)".

OTHER PUBLICATIONS, change "Sulfaction" to -- Sulfation --.
Change "*passage history*" to -- *Passage History* --.
Change "Eschdrichia" to -- Escherichia --.
Change "of Binding" to -- of Specific Binding --.
Change ";" (semicolon) to -- : -- (colon).
Change "Flavobacterium. meningosepticum" to -- *Flavobacterium meningosepticum* --.
Change "1. J." to -- I. J. --.
Change "1." to -- I. --.
Change "yello" to -- yellow --.
Change "169:512-8" to -- 169:512-518 --.
Change "neutrlization" to -- neutralizing --.
Change "virust type2" to -- virus type 2 --.
Change "Analysis of glycogonjugates" to -- Analysis of Glycosaminoglycans with Polysaccharide Lipases --.
Change "application" to -- applications --.
Change "(1997)" to -- (1996) --.
Change "(196)" to -- (1996) --.
Change "end points" to -- endpoints --.
Change "A" to -- Å --.
Change ""," to -- ," --.
After "adherence" insert -- to --.
Change "19: 374-377" to -- 19 : 374-377 --.
Change "mexican" to -- Mexican --.
Change "postischernic" to -- postischemic --.
Change "Diplococcus pneurnoniae" to -- *Diplococcus pneumoniae* --.

UNITED STATES PATENT AND TRADEMARK OFFICE
CERTIFICATE OF CORRECTION

PATENT NO. : 6,197,568 B1
DATED : March 6, 2001
INVENTOR(S) : Rory M. Marks et al.

It is certified that error appears in the above-identified patent and that said Letters Patent is hereby corrected as shown below:

OTHER PUBLICATIONS (cont'd),
Change "E. "Introduction" to -- E. Introuduction --.
Change ""Cellular receptors for animal viruses" to -- "Cellular receptors for animal viruses" --.

Signed and Sealed this

Twenty-third Day of April, 2002

Attest:

JAMES E. ROGAN
Attesting Officer  *Director of the United States Patent and Trademark Office*

UNITED STATES PATENT AND TRADEMARK OFFICE
CERTIFICATE OF CORRECTION

PATENT NO. : 6,197,568 B1  
DATED : March 6, 2001  
INVENTOR(S) : Rory M. Marks et al.

It is certified that error appears in the above-identified patent and that said Letters Patent is hereby corrected as shown below:

<u>Title page,</u>  
Under "*Assistant Examiner*" delete "Feman" and substitute -- Zeman -- in its place.

Signed and Sealed this

Fourteenth Day of May, 2002

*Attest:*

JAMES E. ROGAN  
*Attesting Officer*  
*Director of the United States Patent and Trademark Office*